(12) United States Patent
Siann et al.

(10) Patent No.: US 11,596,263 B1
(45) Date of Patent: Mar. 7, 2023

(54) CONTAINER CONTROLLED ENVIRONMENT SYSTEMS AND METHODS

(71) Applicant: PENDRAM, INC., San Diego, CA (US)

(72) Inventors: Jonathan Siann, San Diego, CA (US); Wilson C. Ng, San Diego, CA (US)

(73) Assignee: PENDRAM, INC., San Diego, CA (US)

( * ) Notice: Subject to any disclaimer, the term of this patent is extended or adjusted under 35 U.S.C. 154(b) by 344 days.

(21) Appl. No.: 15/930,811

(22) Filed: May 13, 2020

Related U.S. Application Data

(60) Provisional application No. 62/847,739, filed on May 14, 2019.

(51) Int. Cl.

| | |
|---|---|
| *A47J 36/24* | (2006.01) |
| *B65D 81/18* | (2006.01) |
| *A47J 36/32* | (2006.01) |
| *G05B 19/042* | (2006.01) |
| *A61L 2/24* | (2006.01) |
| *A61L 2/07* | (2006.01) |
| *A61L 2/10* | (2006.01) |
| *A61J 9/06* | (2006.01) |

(52) U.S. Cl.
CPC ......... *A47J 36/2433* (2013.01); *A47J 36/321* (2018.08); *A61L 2/07* (2013.01); *A61L 2/10* (2013.01); *A61L 2/24* (2013.01); *B65D 81/18* (2013.01); *G05B 19/042* (2013.01); *A61J 9/0646* (2015.05); *A61J 2200/42* (2013.01); *A61J 2200/44* (2013.01); *A61L 2202/11* (2013.01); *A61L 2202/122* (2013.01); *A61L 2202/14* (2013.01); *A61L 2202/15* (2013.01); *A61L 2202/23* (2013.01); *G05B 2219/23258* (2013.01); *G05B 2219/2644* (2013.01)

(58) Field of Classification Search
CPC ..... A47J 36/2433; A47J 36/2438; A61L 2/07; A61L 2/10; A61L 2/24; A61L 2202/23; B65D 81/18
See application file for complete search history.

(56) References Cited

U.S. PATENT DOCUMENTS

| | | |
|---|---|---|
| 5,351,855 A | 10/1994 | Nelson et al. |
| 5,444,984 A | 8/1995 | Carson |

(Continued)

*Primary Examiner* — Timothy C Cleveland
(74) *Attorney, Agent, or Firm* — Barcelo, Harrison & Walker, LLP

(57) ABSTRACT

Systems and methods including a container assembly configured to maintain a controlled environment for storing a product therein are disclosed. Controlled environmental parameters may include at least one of the following: temperature, humidity, payload moisture content, solar radiation, magnetism, microwave, or light illumination. In certain implementations, the system includes a payload chamber and a self-contained environmental control unit (ECU) that may be coupled to the payload chamber using a substantially airtight seal. In certain embodiments, the ECU may include a condenser, a humidity controller, a liquid tank and a power source. Certain embodiments may include a warmer, temperature and/or humidity sensors, and/or a lock. Various combinations of the foregoing components and features may be incorporated, depending on the requirements of each particular implementation.

12 Claims, 28 Drawing Sheets

Controlled Environment System

(56) References Cited

U.S. PATENT DOCUMENTS

| | | | |
|---|---|---|---|
| 5,741,444 A | | 4/1998 | Kasuli |
| 5,934,773 A | | 8/1999 | Ferrell |
| 5,970,719 A | * | 10/1999 | Merritt .................... F25B 21/04 62/3.2 |
| 5,970,987 A | | 10/1999 | Barreiro, Jr. |
| 6,094,917 A | | 8/2000 | Sundhar et al. |
| 6,116,029 A | | 9/2000 | Krawec |
| 6,209,717 B1 | | 4/2001 | Flynn |
| 9,516,972 B2 | * | 12/2016 | Shields .................... A47J 36/24 |
| 9,981,790 B1 | | 5/2018 | Ost et al. |
| 10,107,547 B1 | * | 10/2018 | Kraminer .............. F25D 31/007 |
| 10,443,908 B2 | * | 10/2019 | Kawasaki ............. F25D 31/007 |
| 2003/0183380 A1 | | 10/2003 | Youn |
| 2004/0140304 A1 | * | 7/2004 | Leyendecker ...... A47J 36/2433 219/521 |
| 2007/0012796 A1 | | 1/2007 | Pohl |
| 2008/0093357 A1 | * | 4/2008 | Norman ................. B65D 81/34 219/521 |
| 2010/0012739 A1 | | 1/2010 | Hoeth |
| 2010/0312397 A1 | | 12/2010 | George |
| 2017/0234564 A1 | | 8/2017 | Goel et al. |
| 2019/0133165 A1 | | 5/2019 | Schmitz |
| 2019/0231121 A1 | * | 8/2019 | Alexander .......... A47J 36/2438 |

* cited by examiner

Agitator Position Sensing

Agitator Arm Assembly

Heat Pump – Control Algorithm

CONTAINER CONTROLLED ENVIRONMENT SYSTEMS AND METHODS

CROSS-REFERENCE TO RELATED APPLICATION

This application claims the benefit of Provisional Application Ser. No. 62/847,739 filed on 14 May 2019, the contents of which are herein incorporated by reference in their entirety for all purposes.

BACKGROUND OF THE DISCLOSURE

1. Field of the Disclosure

The disclosure relates generally to systems and methods for providing a controlled environment for object storage, and more particularly to self-contained controlled environment storage and enhancement systems and methods with improved features and characteristics.

2. General Background

Various containers have been developed to facilitate storage of items. Typical storage containers/vessels include the storage container itself and a removable lid. Various modes of interaction of storage containers and associated lids are known.

In certain applications, there is a need to maintain items in a controlled environment in terms of, for example, temperature, humidity, odor control, and/or safety when they are stored in a container assembly.

It is desirable to address the current limitations in this art.

BRIEF DESCRIPTION OF THE DRAWINGS

By way of example, reference will now be made to the accompanying drawings, which are not to scale unless otherwise indicated.

DETAILED DESCRIPTION

Figure 1:
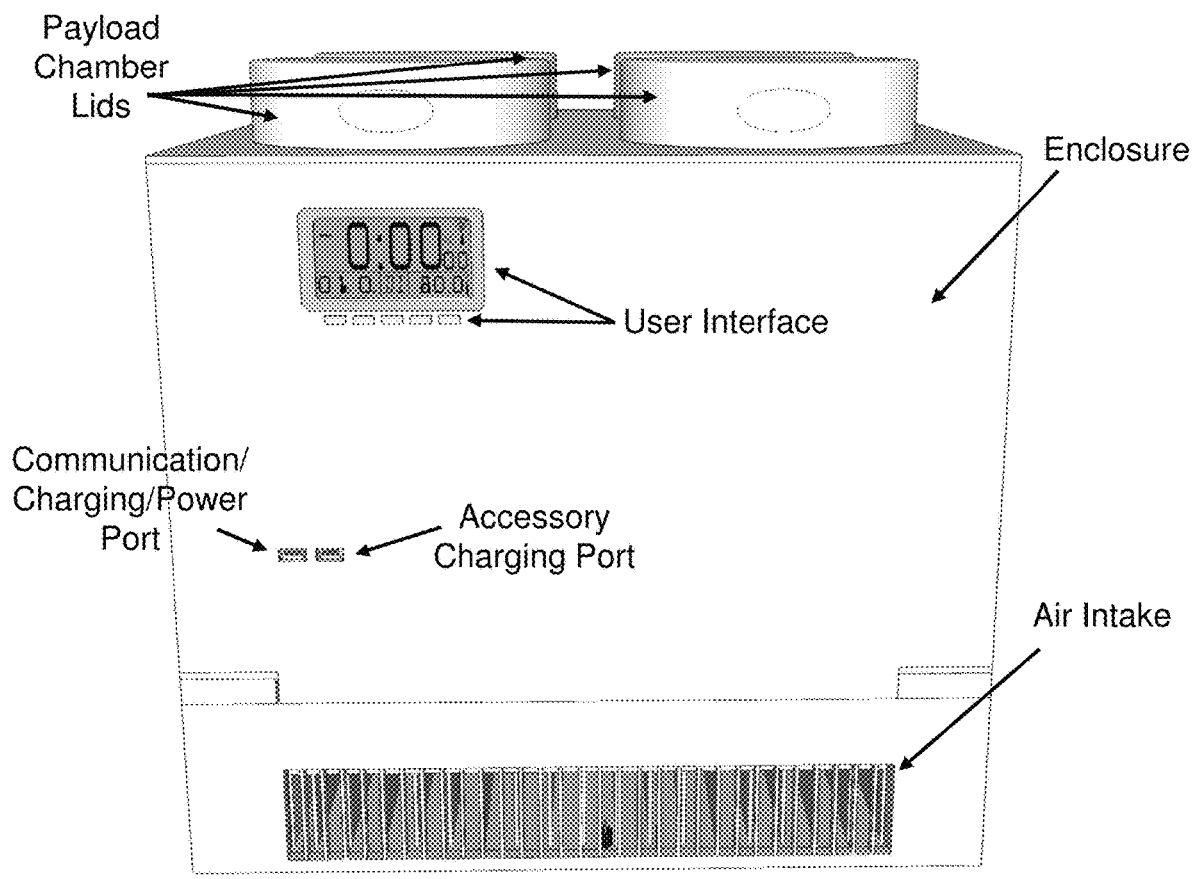
FIG. 1 is an exemplary diagram of a controlled environment system that may be used to implement aspects of certain embodiments of the present invention.

Those of ordinary skill in the art will realize that the following description of the present invention is illustrative only and not in any way limiting. Other embodiments of the invention will readily suggest themselves to such skilled persons, having the benefit of this disclosure, and the general principles defined herein may be applied to other embodiments and applications without departing from the spirit and scope of the present invention. Thus, the present invention is not intended to be limited to the embodiments shown, but is to be accorded the widest scope consistent with the principles and features disclosed herein. Reference will now be made in detail to specific implementations of the present invention as illustrated in the accompanying drawings. The same references and reference numbers will be used throughout the drawings and the following description to refer to the same or like parts.

1 Introduction

The benefits of breast milk are numerous. Breast milk contains antibodies that help babies resist infections and fight off viruses and bacteria. It also contains a nearly ideal mix of vitamins, proteins, and fats that a baby needs to grow. Breast milk has been shown to reduce the risk of developing asthma or allergies. With all the benefits that breast milk provides, not all parents provide breast milk to their babies for the recommended time periods. This may be due to the inconvenience of storing breast milk and/or prepping the breast milk for feeding times, such as during the middle of the night. Current technologies do not seem to allow for the storage and preparation of breast milk within the same enclosure nor for the automated care and preparation that may be provided by a controlled environment system. Current technologies do not seem to provide precise temperature control nor the ability to quickly and efficiently warm the milk. They may need water to be frequently added to the warmer, they may overheat the milk or not heat it enough requiring more interaction and time to reach the desired conditions. Mechanical timers may fail, heating elements may become scaled or fouled, etc. Many parents and care providers give up on using breast milk and turn to using formula due to the inconveniences. By making it more convenient for parents and other care providers, timely preparation of breast milk, it is hoped that the percentage of parents utilizing breast milk may be increased.

A controlled environment system according to aspects of the present invention is a self-contained storage, preparation, and/or enhancement system for organic and/or non-organic objects that may benefit from a controlled environment. Suitable organic objects may include, without limitation, plants, herbal medicines, culinary herbs, food products, dried food, fruits, vegetables, flowers, leaves, meat, flours, sugar, cheese, milk, and the like. Suitable non-organic objects may include, without limitation, coatings, paints, paintings, chemicals, metals, and the like, that may benefit from a controlled environment to allow for curing or to prevent oxidation.

Benefits of the controlled environment system according to aspects of the present invention may include timed preparation of stored items to make them ready to use at any time of day, longer storage times based on providing a better environment for storage, drying, ripening and curing items, optimizing flavor, increasing aroma and potency while eliminating or reducing odor, and preventing mold and bacteria growth during long-term storage of payloads. Other applications for the controlled environment system according to aspects of the present invention may include curing meats, preserving artwork (e.g. paintings), preserving documents, and the care of sensitive seedlings. Other applications for the controlled environment system, according to aspects of the present invention, may include multi staged timed preparation of stored items so that a stored product may, for example, be frozen, heated, boiled and then cooled over a single programmable time period.

The system in at least one application is substantially airtight. Airtightness is important in certain embodiments because it prevents contents from oxidizing and allows for better control of the internal environment. Airtightness is also important for preventing odors from exiting the controlled environment and preserving the internal environment, such as for food products Eliminating or reducing odor leakage from the controlled environment is important for many markets, such as paint curing, food preparation in a closed environment, where the odors may be particularly strong or in some cases toxic.

The controlled environment system according to aspects of the present invention may control at least one of the following conditions: temperature, humidity, payload moisture content, solar radiation, magnetism, microwave, light illumination, and the like. The payload chamber environment may be controlled in an effective and power efficient manner in certain embodiments, but in other embodiments may be controlled in a less efficient manner so as to decrease the time to reach target parameters.

2 Architecture

In certain embodiments, the architecture of a controlled environment system according to aspects of the present invention consists of various subassemblies. These subassemblies work together to create a controlled environment for the item(s) (payload) being stored within. Aside from the controlled environment, one of the main goals of the system in certain embodiments is power efficiency so as to maximize battery life and/or time between battery charges.

As can be seen from FIG. 1, the controlled environment system, in certain embodiments, consists of two main units: an enclosure which provides a user interface, electronics, and access to other subcomponents; and one or more environmental control units ("ECUs") whose location may be identified by the presence of payload chambers. The ECUs may be vertical with access from the top or bottom of the enclosure or horizontal with access from one of the sides. They may be at any orientation. An ECU may consist of a payload chamber and associated environmental control hardware. The environmental control hardware, in the example shown, may serve as a receptacle for the payload chamber or be fully or partially integrated with the payload chamber and may control environmental conditions within the payload chamber.

Not shown on FIG. 1, there may be at least one attachable general purpose zip-up storage compartments to allow for the user to store additional baby bottle nipples, spices, or other items, to the controlled environment system. This may be attached by use of Velcro, button attachment, or other means.

The enclosure may also be comprised of at least one inlet port for drawing air in and at least one exhaust port for exhausting air heated or cooled as a byproduct of the controlled environment; and at least one interface port. These interface ports may provide an interface for wired communications, charging of the batteries powering the controlled environment system, or powering a separate accessory (e.g. cell phone, tablet, etc.). There may be other configurations that may include at least one electrical port. Each port may be a USB-style or any other electrical styles. The user interface may be a display with or without a touch screen along with or without input buttons.

Figure 2:
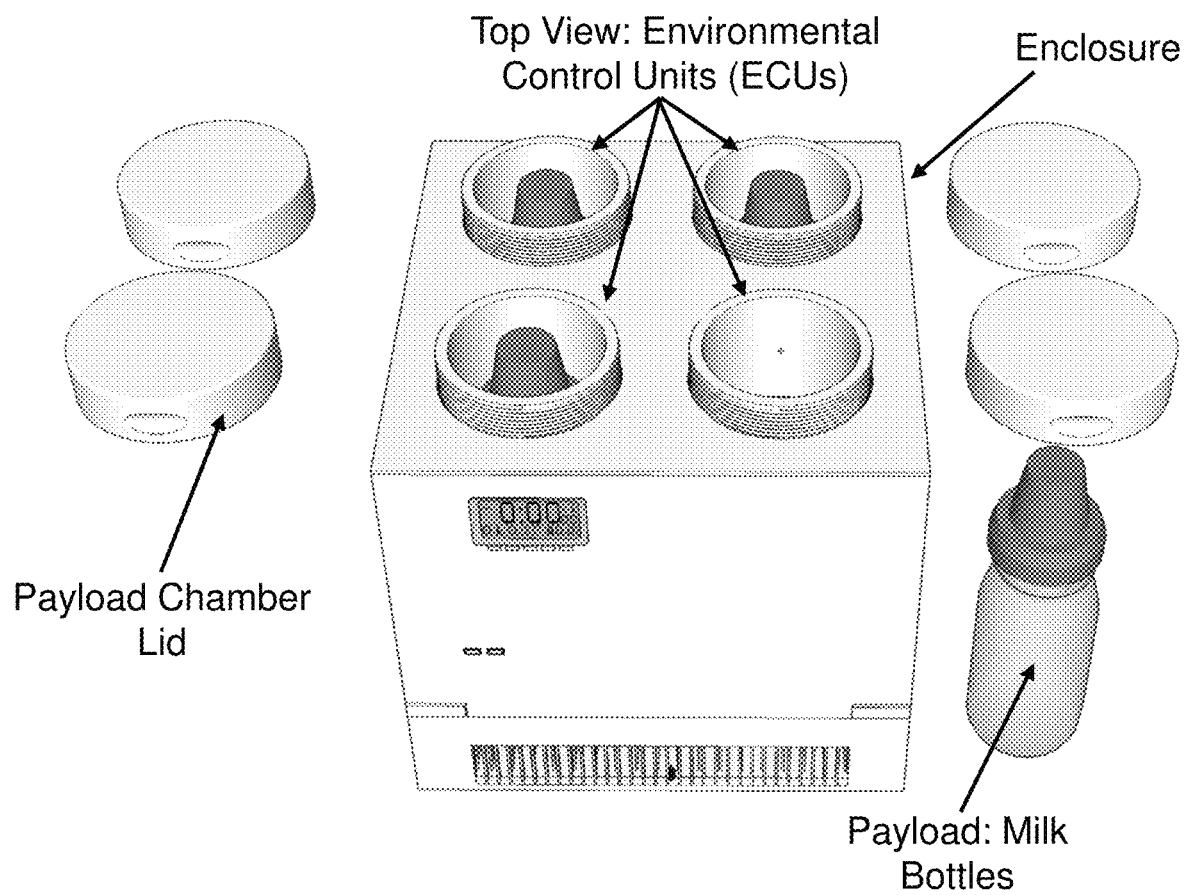
FIG. 2 is an exemplary diagram of a controlled environment system with lids removed and exposed payload that may be used to implement aspects of certain embodiments of the present invention.

FIG. 2 provides a view of the controlled environment system with the lids removed. In this embodiment, there are four ECUs including payload chambers, each for containing a milk bottle payload. The payload chambers may be capable of heating and/or cooling the payload. Payload chambers may have additional functionality such as humidification and dehumidification and are not limited to just temperature and humidity control, other aspects of the environment (e.g. atmospheric pressure, illumination, sound, etc.) may also be controlled. Each ECU may be individually controlled or they may be grouped together into any number of groups. Each payload chamber may contain any type of payload, e.g. juice, carbonated drink, food such as soup or mashed potatoes, etc. Each of the four payload chambers may contain different types of payloads at any one time and each one may be controlled independently of any other. The controlled environment system may contain one or more ECUs including payload chambers.

Controlled environmental parameters may include at least one of the following: temperature, humidity, payload moisture content, solar radiation, magnetism, microwaves, or light illumination. In certain implementations, the system includes an enclosure with one or more environmental control units ("ECUs") that the payload chambers may be placed into. An ECU may be separate from, partially, or fully integrated with the payload chamber. The payload chambers may or may not have a substantially airtight seal, though one may be desirable to reduce energy consumption. In certain embodiments, an ECU may include a condenser, a humidity controller, a liquid tank, and a power source. In other embodiments, an ECU may include heating and cooling apparatus. Certain embodiments may include a heater, cooler, and temperature and/or humidity sensors. Various combinations of the foregoing components and features may be incorporated, depending on the requirements of each particular implementation.

For example, the specific controlled environment system of FIG. 1 and FIG. 2 may be a primarily plastic enclosure with lids whose mating surfaces may substantially separate the payload chamber environment from the external environment. The external surfaces of the enclosure may be lined with leather, painted, stained, etc. The enclosure itself may also fit with or work together with yet other enclosures where multiple smaller enclosures may be fitted together. A lid may be attached to the payload chamber by screwing, bolting, etc. Each lid may be a different type of lid, such as a plastic lid, a metal lid, a transparent lid, a rubber lid, etc. The lid may be round as shown in FIG. 2 but may also have different shapes; such as, square, rectangular, triangular, etc. A lock or latching mechanism may be used to hold a lid closed. The payload chamber may also be used without a lid in certain applications such as boiling or freezing soup, or other food products. Those skilled in the art would find it obvious that other mechanisms and architectures may be used at the mating surfaces to improve isolation.

A lid may have a one-way valve vent hole associated with it to allow pressure and/or steam to escape the payload chamber and may not allow the external environment to pass back through. The lid may also incorporate an array of one or more UVC LEDs to allow for sterilization of the payload chamber and payload contents. The LEDs may also be placed in the payload chamber itself.

Figure 3:
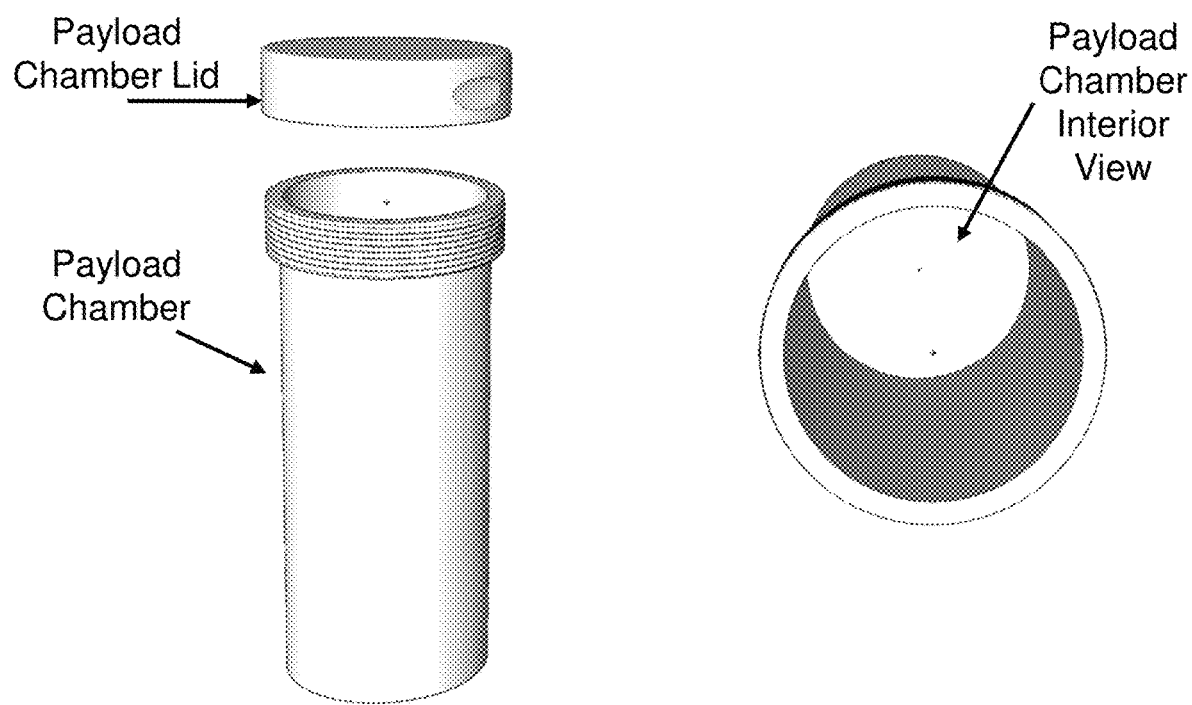
FIG. 3 is an exemplary diagram of a payload chamber that may be used to implement aspects of certain embodiments of the present invention.

Payload chambers may be removeable from the controlled environment system to allow for cleaning and/or servicing. An example payload chamber is shown in FIG. 3. The payload chamber may be made of any material, whether plastic, glass, double glazed glass, metal, wood, composite, or other. It may be any color; whether painted, transparent, or with tint being incorporated as part of the material mix. The payload chamber may also be any size or shape. Payload chambers may contain various methods to sterilize the payload. One method may be to boil the contents and another may be to use UV light LEDs to sterilize the payload.

Aspects of the architecture and the different subassemblies in certain embodiments will be discussed below.

2.1 Subassemblies 2.1.1 Payload Chamber

The payload chamber, shown in FIG. 3, may be a removable subassembly of an ECU and may be any variety of space that may be separated from the environment external to it. The separation may range from complete isolation (temperature, humidity, gasses, solar radiation, light illumination, EMI, etc.) to only partial isolation (e.g. an uninsulated, clear container that may allow humidity, air, light, or temperature to follow, at least partially, the external environment). There may be multiple shorter payload chambers that are stacked together. There may also be multiple payload chambers that are located side by side such as multiple elongated test tubes within the same ECU. Each payload chamber may be any shape and size, or made from any material.

The materials that the payload chamber may be composed of include, but are not limited to, glass, double glazed glass, ceramic, plastic, wood, stone, rubber, metal, leather, or any other materials or combinations thereof. The type of material may be chosen for its cost properties, insulative properties, thickness, aesthetics, weight, a combination of properties, or other.

The payload chamber may enclose items that require a controlled environment. These may include organic substances (e.g. baby bottles, herbs, wood, plants, leaves, vegetables, fruits, soup, soda etc.) or non-organic substances (metals, plastics, films, etc.) that require control of one or more aspects of their environment.

In the exemplary implementation depicted in FIG. 3, the payload chamber consists of a cylinder with threads for a screw on lid. The lid may or may not be insulated. A child safety cap configuration or other press and twist method may also be used to hold the lid to the container. Many approaches would be evident to those skilled in the art and the design is not limited to those mentioned here. The payload chamber may have a window that may be made of glass or plastic, and may be transparent, stained or painted any color. Sensors may be integrated into the payload chamber to track payload usage (e.g. weight, mass, level, etc.) and/or condition (e.g. ready to use, frozen, liquid, contamination presence, etc.). The sensors may be battery powered, remotely powered (e.g. NFC), or powered from the main enclosure supply.

Payload chambers and/or payload chamber lids may also have custom logos added to them by adhering labels, painting, embossing or by any other attachment process in the manufacturing of the enclosure or after the manufacturing of the payload chamber and/or payload chamber lids. The payload chamber and/or payload chamber lids may even be manufactured with the logo built into the enclosure material or some combination of materials.

The shape of the payload chamber may be either dependent, partially dependent, or independent of the item to be stored inside. The payload chamber may be any suitable size and may even be any geometric shape such as circular, rectangular, square, triangular, etc. The payload chamber may be partially or fully inserted into the controlled environment system enclosure. The payload chamber may have one or more items and types of items stored within.

Figure 4:
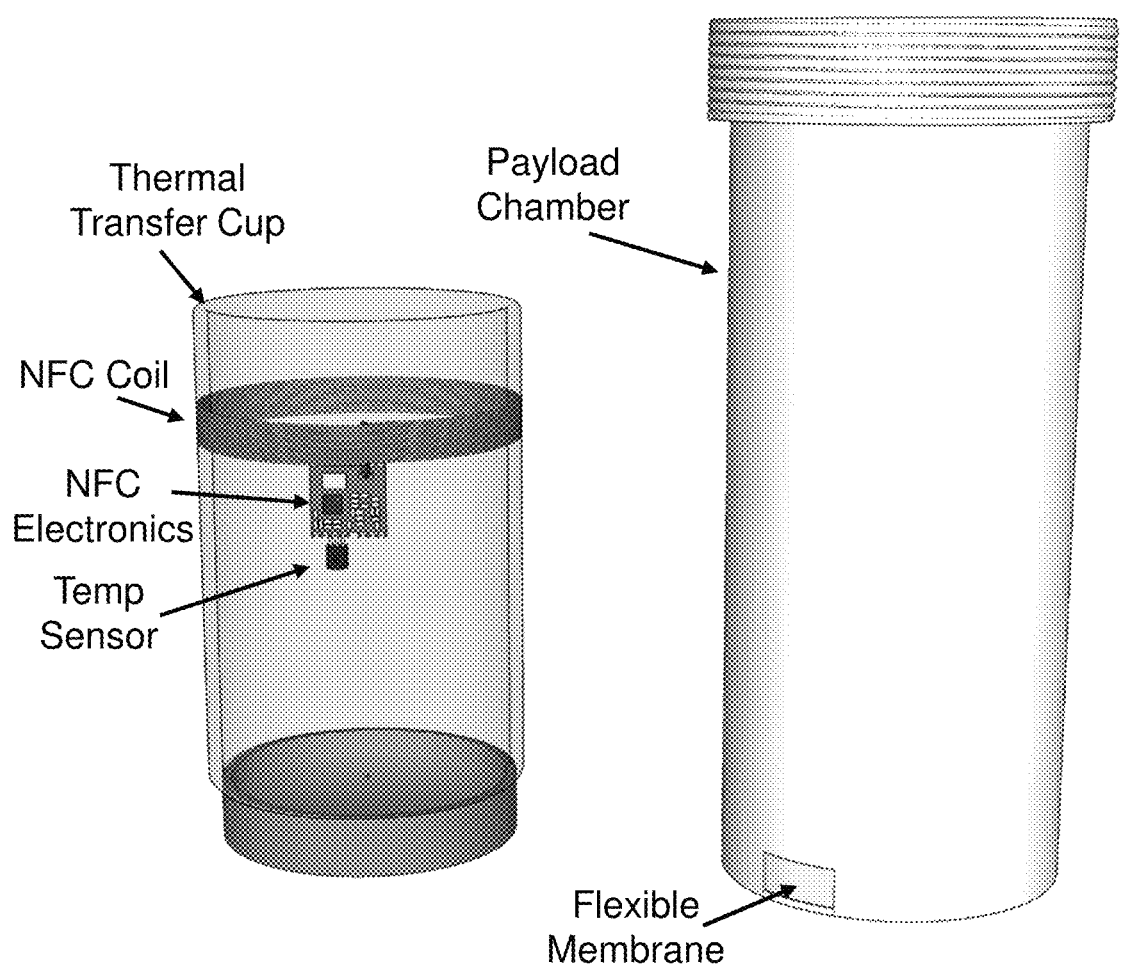
FIG. 4 is an exemplary implementation of a payload chamber and thermal transfer cup that may be used to implement aspects of certain embodiments of the present invention.

The payload chamber may have one or more openings within it to allow for viewing, and/or external objects to poke in or be inserted. FIG. 4 shows the opening in the bottom of the payload chamber covered with an elastic membrane that may allow the agitator arm to push in but, at the same time, not allow payload chamber items to come out.

Figure 5:
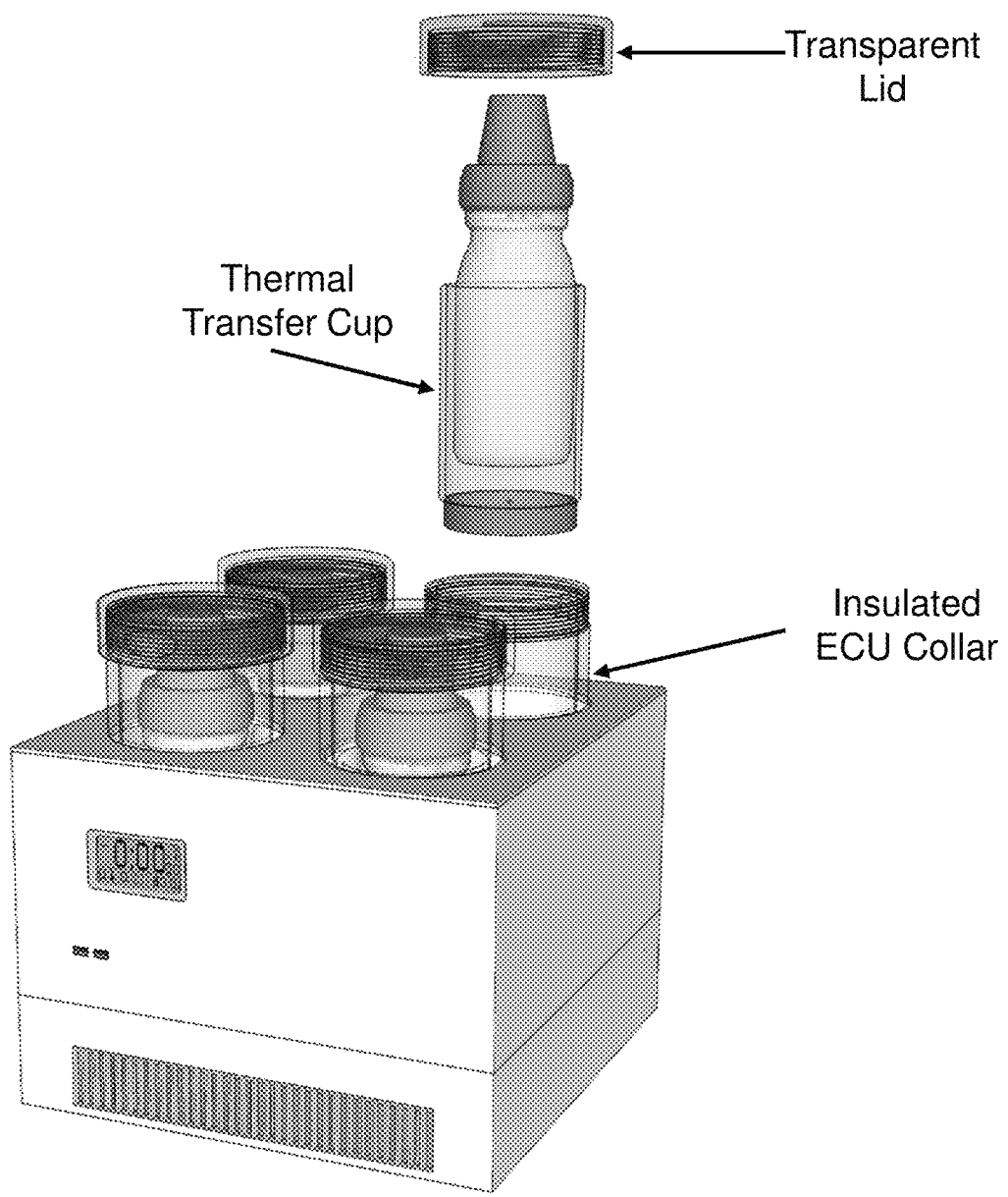
FIG. 5 is an exemplary implementation of a controlled environment system with transparent payload chamber components that may be used to implement aspects of certain embodiments of the present invention.

FIG. 5 shows an alternative embodiment of a controlled environment system enclosure which makes the payload chamber transparent and allows the user to view the contents without opening the payload chamber. This embodiment may utilize the same components as the previously discussed embodiment with the differences of transparent, insulated lids and/or transparent payload chambers, taller or shorter payload chambers which may be combined with a reduced height enclosure, and an insulating ECU collar to expose more of the payload. Multi-colored LED lighting may be incorporated into the transparent payload chamber so as to indicate ECU and payload status (e.g. heating, cooling, idle, ready, etc.). LEDs may also be incorporated into one or more sides of the enclosure for rapid determination of status.

2.1.1.1 Payload Chamber Liner

The payload chamber may also be lined with a removeable liner and/or contain one or more thermal transfer cups, see FIG. 4. The cup may be an enclosed gel liner with good thermal transfer characteristics which acts as a shim between the walls of the payload chamber and the payload. This may allow for the payload chamber to be adaptable to different size payloads as well as to enhance the flow of thermal energy between the environmental control unit's heat conducting shell (FIG. 17), which the payload chamber fits into, and the payload. Different sized or shaped cups may be used to adapt to different sized or shaped payloads. The removeable liner and/or thermal transfer cups may be stretchable and conformable to the shape of the payload for enhanced thermal energy transfer.

The liner may be water tight so that a payload may be directly inserted into it and either cooled or heated without a container. The thermal transfer cup (may also be referred to as a liner or heat transfer jacket (HTJ)) may be integrated with near field communication (NFC) capabilities and a temperature sensor to communicate payload temperature information to the main controller. The payload chamber itself may also be integrated with NFC capabilities and a temperature sensor to communicate payload temperature information to the main controller. The removeable liner and the payload chamber may be easily washed in a dishwasher or may be washed by hand.

The thermal transfer cup, or liner, may include one or more NFC coils to gather energy sent to it via the ECU, shown in FIG. 4. The energy may be collected by the NFC electronics and used to power one or more sensors and report back the readings of the sensors to the enclosure controller. Sensors may be placed on or in the liner, on or in the payload chamber or anywhere on or inside the controlled environment system, and may include, but are not limited to, temperature, sound, micro-electro-mechanical systems (MEMS), gyro, accelerometer, etc. A remote temperature sensing capability may allow for finer control of the payload temperature as well reduce the energy usage of the controlled environment system. An accelerometer may allow the system to determine that the system is tilted, being shaken, etc. An accelerometer may also allow the system to determine if any of the individual or groups of payload chambers are being tilted, shaken, etc.

The thermal transfer cup may have a solid base so that tapping from the agitator arms may more readily be communicated to the payload. The thermal transfer cup is not limited to a solid base and many other techniques may be obvious to those skilled in the art for allowing the tapping vibrations to proceed to the payload.

2.1.2 Enclosure

Figure 6:
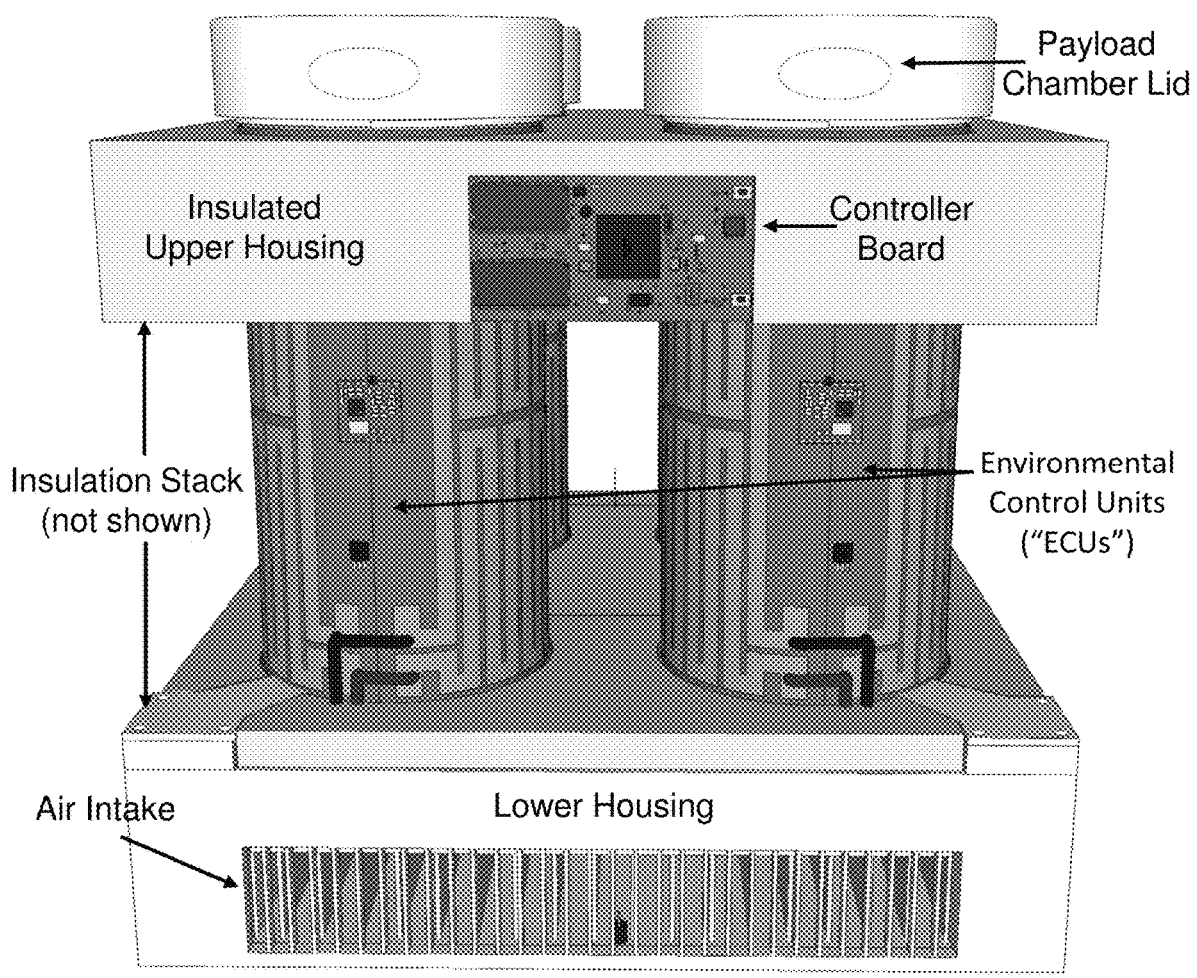
FIG. 6 depicts a controlled environment system, with the enclosure walls removed, exposing internals that may be used to implement aspects of certain embodiments of the present invention.

One or more payload chambers may fit into their associated ECUs in the enclosure. As can be seen in FIG. 6, the payload chambers drop into the upper portions of the environmental control units ("ECUs"), which themselves may be part of the enclosure. An enclosure may have any number of ECUs and is only limited by the desired size of the enclosure. The enclosure of the embodiment shown has upper and lower housings. The upper housing provides support for the ECUs, insulation between ECUs, and may also provide a location for a controller board. The lower housing provides support for the bottom of the ECUs and may also contain power sources and associated circuitry, heat exchangers, sensors, actuators, exhaust opening, and fans, as well other components. Between the upper and lower housings, not shown for clarity of the ECUs, may be thermal insulation filling all or some of the empty space between the upper and lower housings.

The housings may be manufactured using any materials, as previously mentioned. They may even be made from a transparent material that allows the user to view the payload contents from outside the unit.

Between each payload chamber and between the upper and lower housings, may be insulating material. This may be any thermal insulating material; such as, cork, cotton, Polyisocyanurate (also referred to as PIR, polyiso, or ISO) which is a thermoset plastic that can tolerate the high temperatures needed for the sterilization mode (100 C or higher), Polyurethane, sometimes employed as a sprayable foam based material, etc. The insulation may have a honeycomb pattern, or a layered pattern, or any other pattern and may or may not be combined with air within the patterns such that air adds to the insulative properties. An alternative to the insulating material may consist of a vacuum sealed shell or housing.

In some embodiments, an enclosure may consist of only one or two ECUs. Additional enclosures may be ganged together with the first and operate as part of a group or may be operated independently. Enclosures may be magnetically coupled together or coupled using other options (screws, cables, glue, etc.). Enclosures may also be stacked together if needed. Any number of enclosures may be used and created into any geometric shape.

2.1.2.1 Controller Board

A generic microcontroller board, also shown in FIG. 6, is utilized for executing the firmware for managing ECU operations, controlling charging via the power management unit ("PMU"), monitoring sensors, generating alarms, communications with external devices, and providing a user interface among other tasks. The controller board may be similar to the ESP32 from Espressif Systems. The microcontroller board may be comprised of more than one board within the Controlled Environment System.

The controller board may contain various hardware and software components, such as, flash, RAM, switches, a microcontroller, wired and wireless interfaces and associated ICs, power devices and other standard devices that may be found on such a board. The microcontroller board may also contain motion and gravity sensors such as gyros, accelerometers, etc. to detect and respond to motion of the Controlled Environment System. Given the presence of wireless communication components on the microcontroller board (e.g. WLAN, Bluetooth, NFC, cellular, etc.) antennas may be included on the board or interface to the board.

The controller board may include GNSS (GPS) and/or other functionality that establishes location. It may also include a connection mechanism, such as, a cellular modem, WiFi interface, etc. to allow the unit to communicate its position as well as connect to the Cloud for data exchange.

The controller board may be capable of keeping accurate time, even when main power is disconnected and may also retrieve an accurate time by potentially using Network Time Protocol (NTP) or other means when connected to a network. The controller may use the time to set multiple event timers for controlling actions of the various ECUs, such as when to start warming baby milk, when to start the next bottle, etc. and may also be in charge of generating notifications to the user when items become ready.

2.1.2.2 Power Sources

Figure 7:
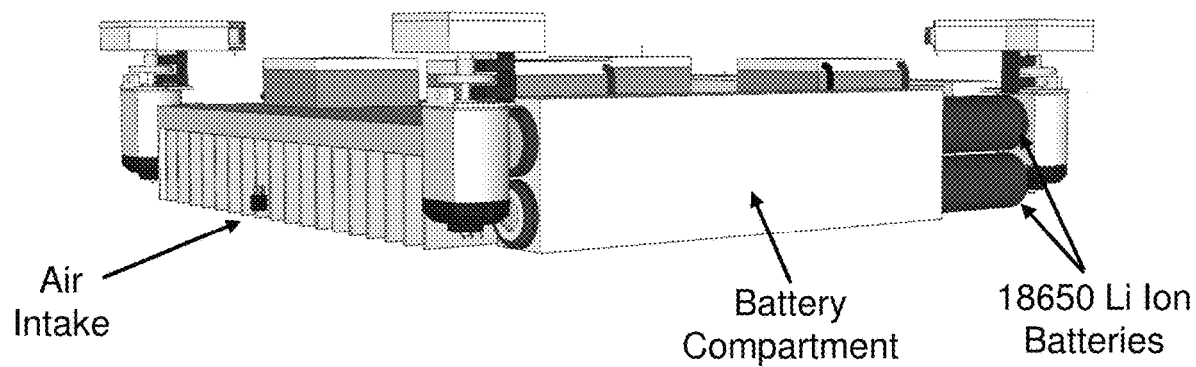
FIG. 7 is an exemplary diagram of battery location within a controlled environment system enclosure that may be used to implement aspects of certain embodiments of the present invention.

The system may be powered, see FIG. 7, from internal batteries located in the lower housing (FIG. 6), either rechargeable or primary replaceable, and/or from external power. External power may be brought in via a connector port (power port) as shown in FIG. 1 or other types of DC power connectors. The external power input may offload the internal batteries, as well as recharge them if they are rechargeable, all without impacting the unit's operation. The batteries may be user or factory replaceable and as such, user access may be provided. There may be no batteries installed, a single battery installed, or multiple batteries installed within the controlled environment system.

FIG. 7 shows the battery compartment assembly which secures the batteries in their positions. The assembly may also provide structural support to the enclosure.

2.1.2.2.1 Power Management Unit (PMU)

The Power Management Unit (PMU) may be a part of the controller (microcontroller) board or the microcontroller, or on a separate board within the Controlled Environment System. The power management may also be distributed throughout the enclosure. The PMU may receive energy from the internal batteries as well as the power connector and selects which power source to use for the system. The PMU may be responsive to control from the microcontroller and is also responsible for generating and distributing voltages and current to control the electronics within the enclosure.

The PMU may also be responsible for charging any rechargeable batteries and prioritizing which power source to use as well as generating notifications and alarms when energy levels fall below user set thresholds. The PMU may make the current energy state available to the microcontroller for statistics, reporting, and alarm purposes.

2.1.2.3 Lower Housing

Figure 8:
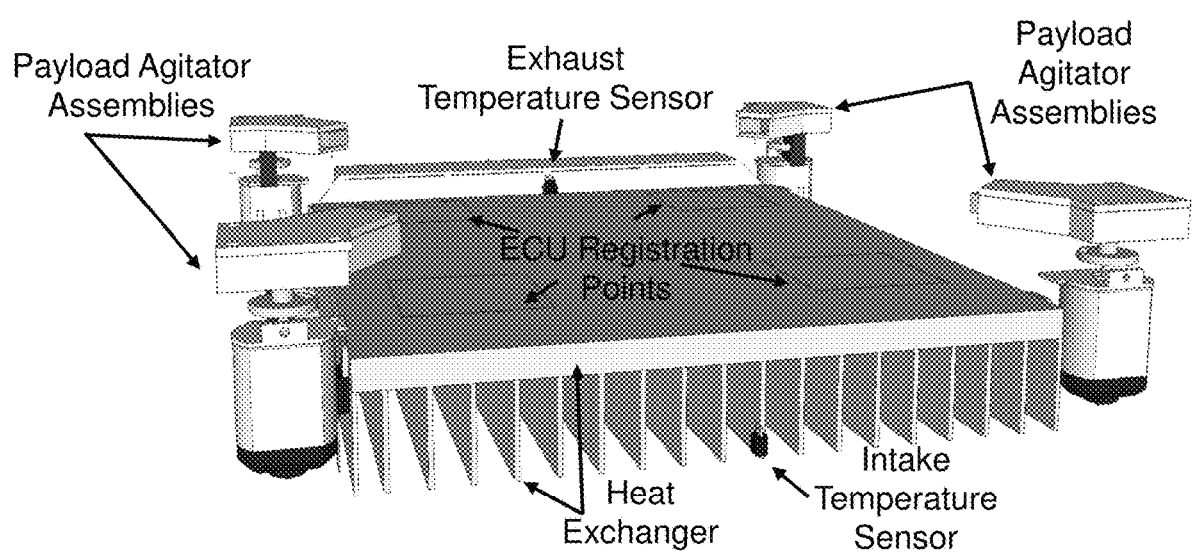
FIG. 8 is an exemplary diagram of the controlled environment system lower housing (frontal view) showing internals that may be used to implement aspects of certain embodiments of the present invention.
Figure 9:
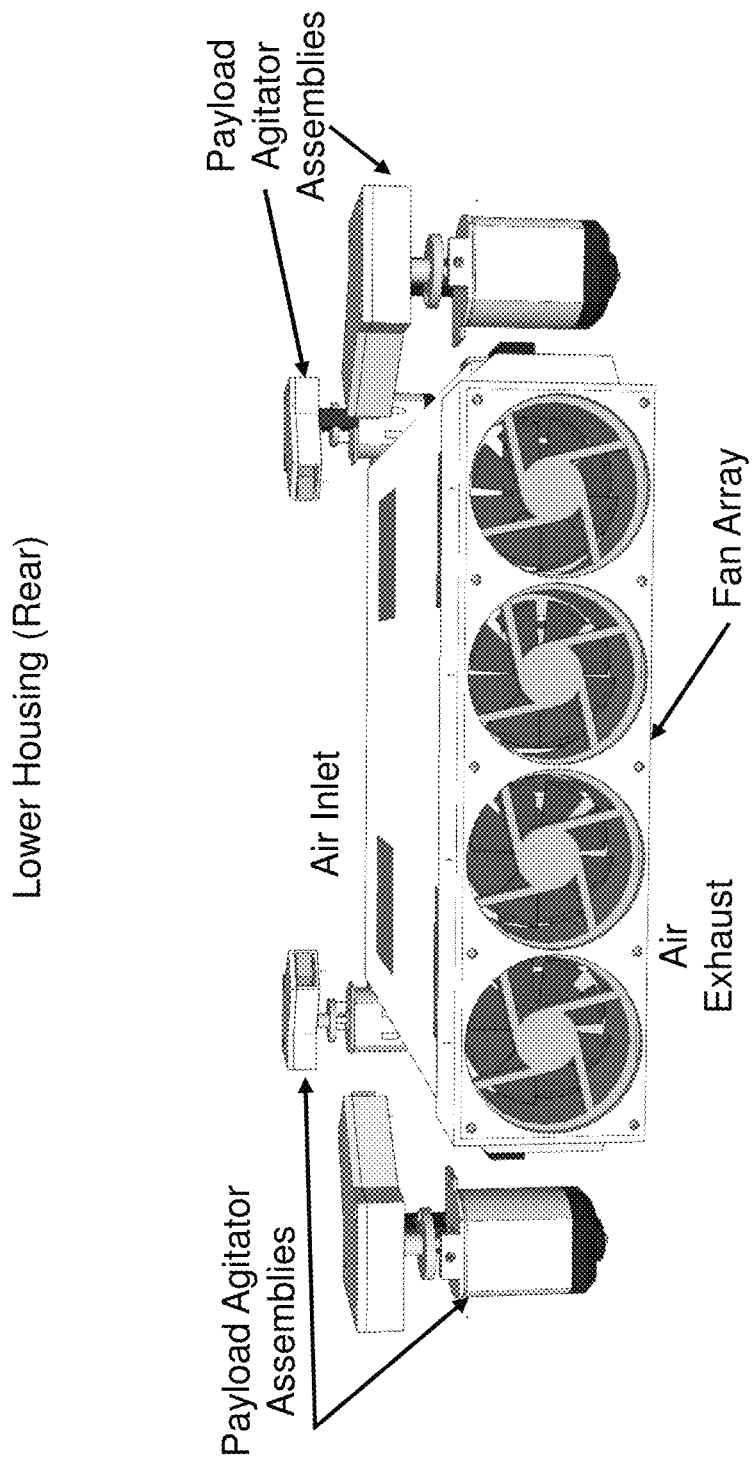
FIG. 9 is an exemplary diagram of the controlled environment system lower housing (rear view) showing internals that may be used to implement aspects of certain embodiments of the present invention.
Figure 10:
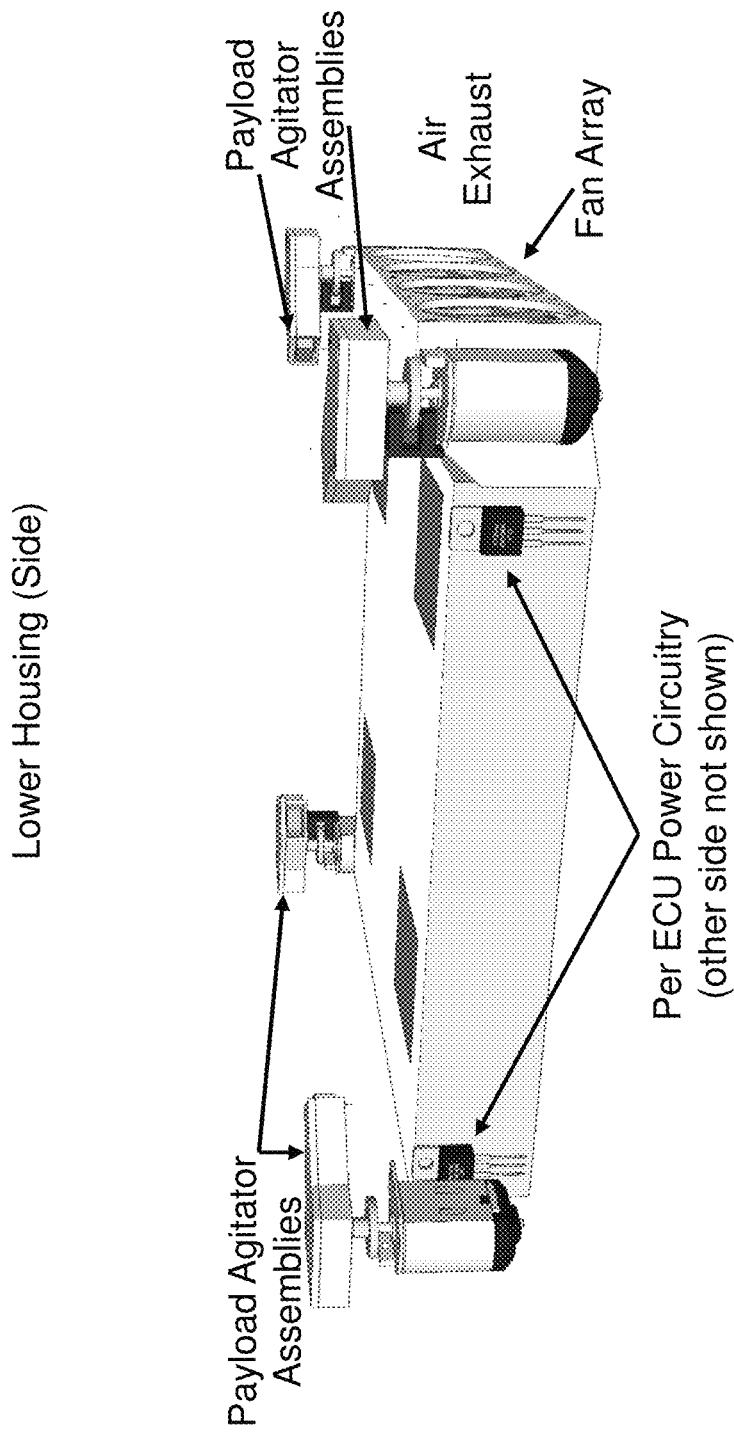
FIG. 10 is an exemplary diagram of the controlled environment system lower housing (side view) showing internals that may be used to implement aspects of certain embodiments of the present invention.

The lower housing of the enclosure contains modules that may be common or shared by the ECUs in a controlled environment system. Shared systems may include, but are not limited to, power supply circuitry, heat exchanger and fans, payload agitators, sensors, etc. FIG. 8 shows some of the shared lower housing components with the batteries and battery compartment removed. FIG. 9 shows a rear view of the lower housing with the fan array visible. FIG. 10 shows a side view of the lower housing exposing the ECU power circuitry. Each ECU may be controlled independently and may be set to perform different tasks.

2.1.2.3.1 Heat Exchanger

As shown in the lower housing embodiment of FIG. 8, a heat exchanger may be shared by the ECUs. Sharing thermal energy between ECUs, such as when one is cooling and another is heating, may improve battery life by reusing thermal energy (heat) removed from one ECU to warm up another, or by taking advantage of thermal energy (heat) removed from the heat exchanger (by warming an ECU) to cool a different ECU. In other embodiments, there may be more than one heat exchanger such that they may be independent or multiple sub-groups of ECUs may share heat exchangers. Each ECU may attach onto the square/rectangular registration points shown. The heat exchanger has one or more sensors associated with it. One temperature sensor may be used to measure the incoming air temperature at the inlet side. Another temperature sensor may be used at the exhaust side so as to measure the temperature of the heat exchanger. The sensor readings may allow the control software to accurately determine the temperature differential across the heat exchanger. This information may be used to control fan speed as well as parameters of the ECUs.

The ECUs, depending on whether operating in a heating or cooling mode, may be pumping heat away from the heat exchanger or into the heat exchanger.

2.1.2.3.1.1 Airflow

A fan or array of fans, FIG. 9, may be used to pump air from the ambient environment and direct it through the paths/ducts created by the heat exchanger fins. The fans may be single speed or variable speed and may be on all the time or used only when required. The fans may be designed to be low noise and may be managed by the microcontroller board so as to increase the overall power efficiency of the Controlled Environment System. Depending on the usage, one or multiple fans may be used. If more than one fan is used, each fan may be completely independent and there may be different types and sizes of fans.

The walls of the lower housing may be constructed of, or lined with, noise dampening materials so as to reduce any acoustic signature of the controlled environment system. Airflow through the heat exchanger is intended to be as smooth and laminar as possible, reducing any turbulence and dead spots, so as to maximize the efficiency of air treatment and correspondingly, consumed power. The walls of the lower housing may be made of any material, be any color, and may be made using transparent material.

In certain embodiments, in order for the ECUs and enclosure to be effective and efficient, as well as to have a low acoustic signature, the air flow through the heat exchanger should be orderly, unidirectional and free of turbulence. Airflow through the heat exchanger fins may be laminar, experiencing few changes in direction and speed. Backflow, where airflows of differing speeds or differing temperatures may be unintentionally mixed, should be avoided. As can be seen in FIG. 8, the air pulled in by the fans may flow smoothly through the fins of the heat exchanger in a laminar manner as the space between fins acts as ducting. Thus, air flow through the heat exchanger is preferably transversal and along the surface area of the fins with minimal air resistance (e.g., laminar), thereby experiencing few changes in direction and speed.

Preventing the mixing of air entering the enclosure with air exiting the enclosure may at least be partially due to the physical relationship of the air inlet and air outlet on opposite sides of the enclosure. As seen in FIG. 9, the enclosure inlet and outlet are extended to the edges of the product, maximizing the distance between the inlet and outlet.

2.1.2.3.1.2 Fan Design

Establishing laminar airflow begins with the use of a transversally mounted fan or fans located at the air outlet, FIG. 9. Note that the fans may either push air into the unit or pull air out of the unit. In the given embodiments, the air is pulled into the unit. With this relationship, the axis of rotation of the fan's propeller is situated to drive air through the ducts created by the heat exchanger fins which smoothly directs the air across the fins, rather than into the base of the heat exchanger. The transversally mounted fans produce airflow substantially along the fins of the heat exchanger. The fins in combination with a covering over any unneeded openings of the fins act as ducts, ensuring air flow through the heat exchanger fins to be at least partially laminar.

Another relevant factor is that the acoustic signature of a fan increases dis-proportionally with the rotational rate of the propeller. To reduce the acoustic signature of the fan, the rotational rate of the propeller within the fan, may be substantially reduced. To maintain the fan's airflow, the angle-of-attack of the propeller blade's airfoil is normally increased. But as angle-of-attack increases, the airfoil becomes inefficient. A low noise design maintains airflow, airfoil efficiency, and utilizes low rates of propeller rotation.

As the fan's thickness may not be constraining, maintaining airflow and airfoil efficiency may be accomplished by substituting increasing the airfoil's angle-of-attack with increasing the airfoil's chord-length.

2.1.2.3.1.3 Fan Control

The fans are controlled by the control board firmware and may be run at one speed, different speeds, or as variable speed fans. The enclosure's ECU Control Algorithm determines the velocity of airflow required through the heat exchanger based on several factors, such as mode (Economy or Turbo), noise level, whether humidity needs to be added to or removed from a payload chamber, the amount of humidity to be added or removed, whether the temperature needs to be changed and how quickly, and to minimize power consumption. In the case of more than one fan, the control algorithm may run the fans at slightly different speeds so as to avoid or reduce audible beat tones.

The rotational rate of the propeller within a fan, is set to produce only as much air flow as necessary to accomplish the required tasks. Determining the optimal amount of air flow may be accomplished by measuring the temperature differential between the inlet and the exhaust. The measurements are provided to the control board which may be running a feed-back control loop that optimally sets the rotational rate of the fan by adjusting its supply voltage.

2.1.2.3.2 Power Circuitry

Attached to the sides of the heat exchanger (FIG. 10) may be power circuitry to supply power to the ECUs, fans, and payload agitator assemblies. By having the circuitry attached to the heat exchanger, the circuitry may run cooler (promoting lifespan), and also promote the efficiency of warming the payload by providing heat that can be pumped to the payload. Additional circuitry may also be mounted to the heat exchanger or elsewhere in the controlled environment system.

2.1.2.3.3 Payload Agitator Assemblies

The enclosure may have at least one payload agitator assembly per ECU. The purpose of an agitator assembly is to tap, stir, spin, or shake the payload; for example, a baby bottle full of milk. By agitating the bottle, the bottle contents may be mixed and the content temperature may be more evenly distributed, whether heating or cooling and can allow for faster warming of the payload without overheating the payload material closest to the heat source. For example, it would allow a parent to more quickly heat milk for a hungry baby while minimizing the potential impairment of the quality and/or nutritional value of the milk. There are many different ways to agitate payload contents. One can use vibrational oscillators under each ECU or under all the ECUs, one can place a lifting and lowering mechanism within each payload chamber to lift and drop the payload, or one can tap or rotate the payload chamber, etc. There are many possible approaches that would be obvious to one skilled in the art.

Figure 11:
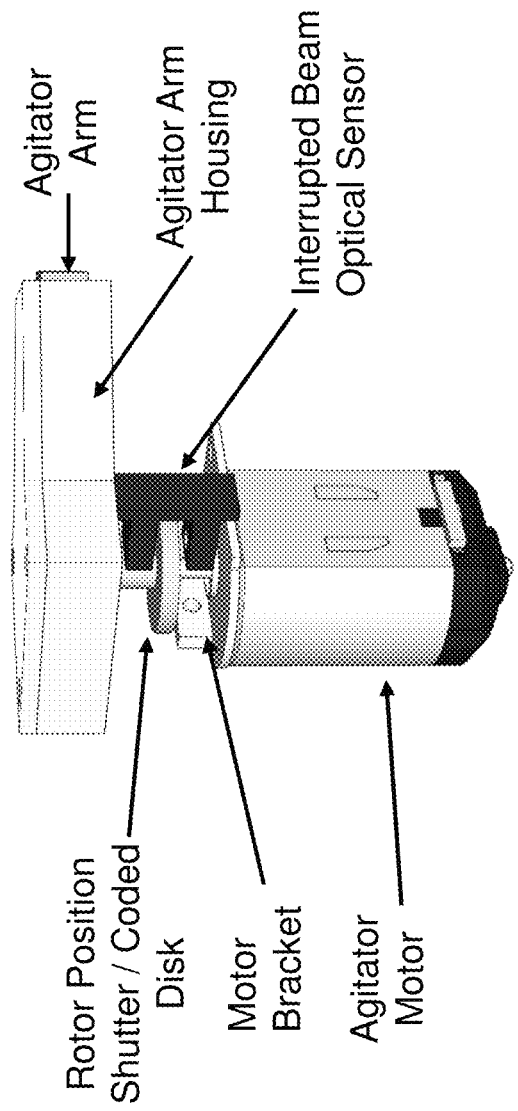
FIG. 11 is an exemplary diagram of a payload agitator assembly that may be used to implement aspects of certain embodiments of the present invention.

The embodiment shown in the figures, (e.g. FIG. 10), shows payload agitators which may be used to generate a tapping motion against one or more of the payloads. FIG. 11 shows the components of the payload agitator assembly. The agitator motor provides the rotational force to move the agitator arm. The motor may be any variety of electric motor, DC or AC, single or variable speed, and free spinning type or stepper or servo types. Any type of motor may be made to function for the purpose but with different impacts on power used, heat generated, and controllability. The motor used in the embodiment shown may be a variable speed DC motor. The rotational rate of the motor may be controlled by an external motor controller which may be part of one of the circuit boards within the enclosure.

Figure 12:
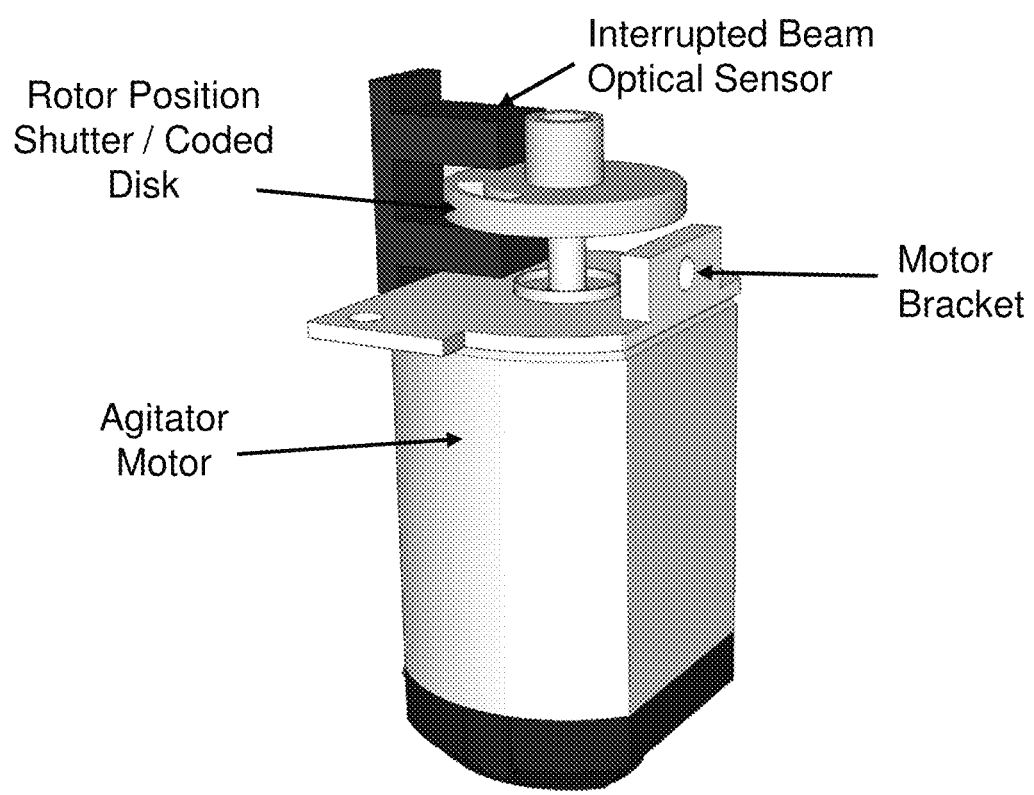
FIG. 12 is an exemplary diagram of agitator position sensing that may be used to implement aspects of certain embodiments of the present invention.

The agitator motor or motors may be attached to the heat exchanger or to the enclosure itself. They may be attached via the motor bracket at the top of the motor, see FIG. 12. FIG. 12 shows a view of the agitator motor assembly with the agitator arm assembly removed to show one possible method to detect the motor's position as well as the motor's rotational rate. As seen in FIG. 12, an interrupted beam optical sensor may be used in combination with a coded disk or rotor position shutter. Whenever the opening in the disk passes the optical sensor, a light beam is able to traverse to the sensor. As stated previously, this may be used to detect the rotational rate of the motor and also the position of the agitator arm. The coded disk may be coded with one or more openings of one or more different sizes.

Figure 13:
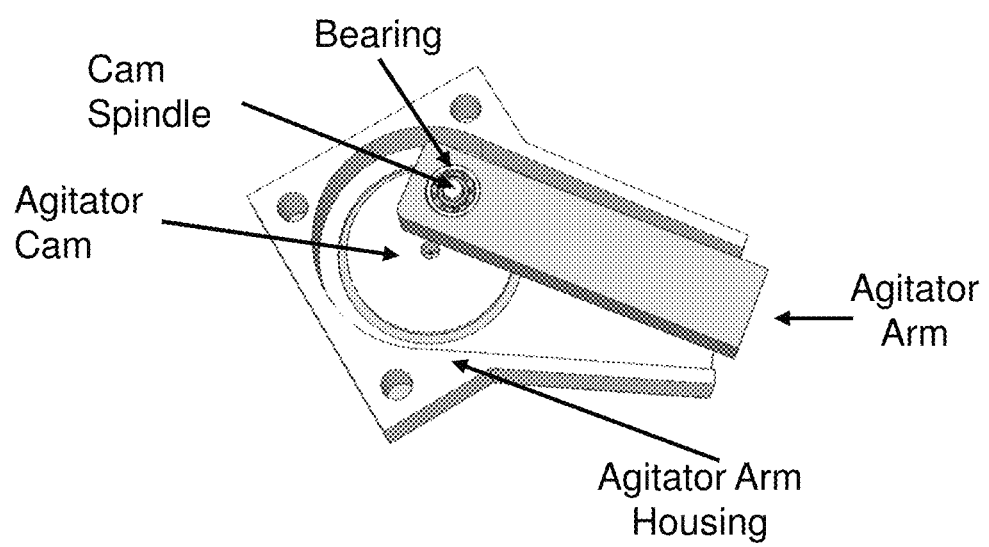
FIG. 13 is an exemplary diagram of an agitator arm assembly that may be used to implement aspects of certain embodiments of the present invention.

FIG. 13 shows an internal view of the agitator arm assembly. In the embodiment shown, the motor rotates the agitator cam. The agitator cam may have a spindle attached to it, or formed as a part of the cam. A bearing may be added to the spindle to provide a reduced friction movement of the agitator arm which is attached to it. As the motor and agitator cam rotate, the agitator arm is pushed out and pulled back in to tap the base of a payload chamber. The material of the agitator cam and arm, as well as the housing, may be made from a lubricant impregnated material or any other material that meets the requirements of the assembly. Many other possible implementations would be obvious to one skilled in the art.

2.1.2.4 Physical User Interface

As can be seen in FIG. 1, the Controlled Environment System onboard user interface mechanism consists of a display screen (either touch sensitive or not), buttons, an accessory charging port, and a communication/charging/power port. In addition to buttons, knobs or other interface mechanisms may also be used for setting parameters. The display may be capable of displaying multiple different settings and monitored parameters, alarms, and status and may be touch sensitive or not. The display technology used may be LED, LCD, OLED, AMOLED, etc. and is not limited to any particular display technology. The display and enclosure may communicate information regarding the conditions within the payload chambers and also present a manner by which a consumer may control the status and/or conditions within the payload chambers. A controlled environment system may respond to and warn of unintentional conditions, such as droppage, breakage, tampering, non-level position, excessive vibration or shock etc. by generating an audible and/or visual signal, either on the unit or a wireless alarm sent to an offsite monitoring solution. The LCD display, instead of being an attached part of the enclosure may also be a remote display that may be connected to the unit either wirelessly or wired and placed on the outside of the enclosure.

FIG. 1 also depicts multiple buttons. The enclosure may contain more or fewer buttons than are depicted and they may be positioned anywhere on the enclosure. The user may input commands and data into the unit by using the buttons or a combination of them and the LCD to program various payload and alarm parameters. The LCD may contain a touch interface that allows information and commands to be input into the touch interface. Any of these aforementioned interfaces may be used to request feedback or provide instructions to generate a history of the environment as well as generate data such as past alarm data.

The user may program the unit remotely as well as locally. Locally may be performed by using the LCD and/or the buttons. Remote programming may be accomplished by connecting an electronic device to the unit either through a wired interface via the communication port or through a wireless interface. The wired and wireless interfaces may also be used for downloading applications, control information, and data, uploading of software or data, and performing firmware updates.

The enclosure may implement one or more wireless interfaces, such as a WiFi interface or other wireless interface (e.g. Bluetooth, Zigbee, BLE, cellular, etc.) so as to be able to interface to user devices such as computers and cell phones as well as databases that may be stored in the Cloud.

The enclosure interface may incorporate biometric security for locking and unlocking configuration access, in addition to a display touchscreen or button type interface where a key sequence is entered. The biometric interface may include a fingerprint reader, eye scanner, facial recognition, or other type of biometric. It may also use a combination of any of the biometric interfaces or the display touchscreen or button interfaces, and may even be integrated into the touchscreen.

A biometric security interface may also be used to obtain access to the Controlled Environment System's data or to be able to control it.

2.1.3 Environmental Control Units

Figure 14:
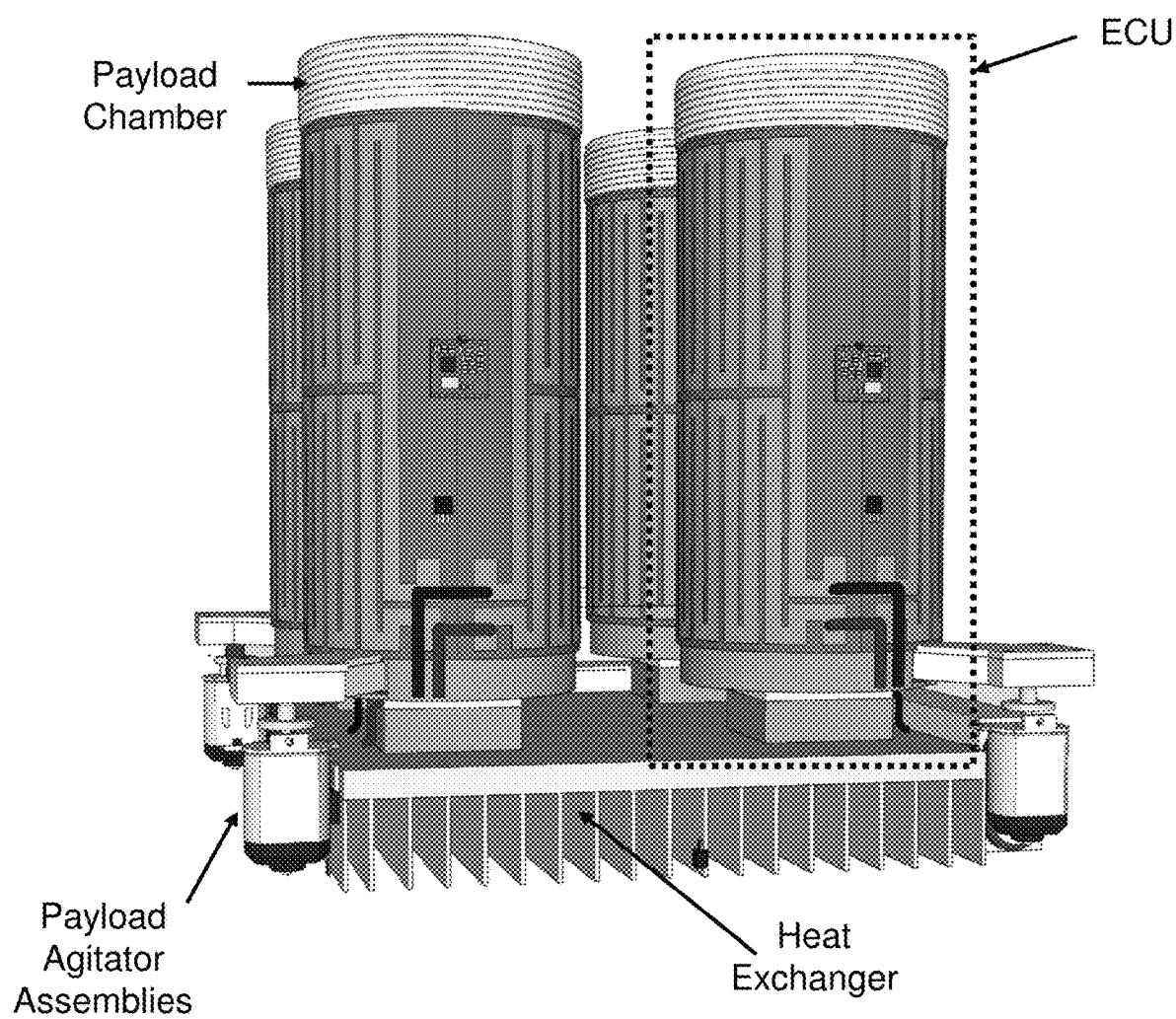
FIG. 14 is an exemplary diagram ECU placement within a controlled environment system enclosure that may be used to implement aspects of certain embodiments of the present invention.

The environmental control units may be controlled by the controlled environment system's controller board. Items that may be controlled may include, but are not limited to, target temperatures, start time, stop time, temperature hold time, warming ramp, cooling ramp, and other aspects of a temperature profile. As stated previously, the ECUs are independent of each other and may be performing different task types. FIG. 14 shows four ECUs and their placement within the enclosure with the shell of the enclosure stripped away. A specific ECU is shown within the dotted rectangle and will be discussed in the following paragraphs and sections. The ECUs may all be of the same type or of different types; for example, one may control temperature while another may control temperature and humidity. The ECUs in the following discussions may only control temperature.

Figure 15:
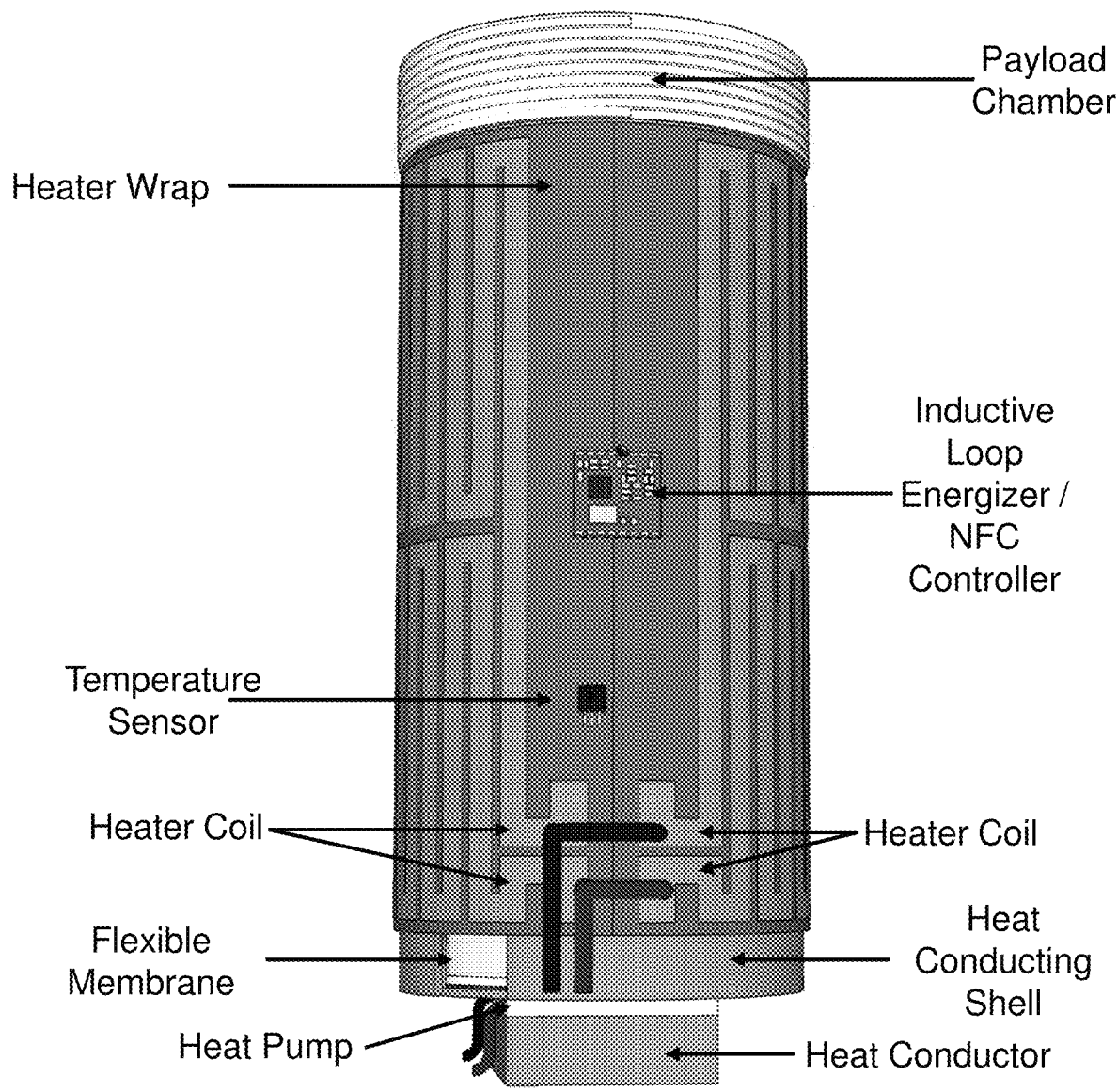
FIG. 15 is an exemplary implementation of an environmental control unit (ECU) that may be used to implement aspects of certain embodiments of the present invention.

An exemplary implementation of an ECU, FIG. 15, may substantially set apart or isolate the internal environment of the payload chamber from the external environment. In addition to isolating the external environment from the payload chamber environment, an ECU is responsible for controlling one or more aspects of the internal environment (e.g. temperature, humidity, light illumination, pressure, sound, etc.). The following subsections will discuss the main components of an ECU.

An ECU may be designed to maximize power efficiency to extend battery life and/or time between charging of the batteries. The controlled environment system may generate a signal to indicate to a user that battery or charge level has decreased to the point requiring changing of the batteries or recharging. The payload chamber, while a part of the ECU assembly, was discussed previously as its own subassembly.

An ECU may be composed of several subcomponents, some of which are shown in FIG. 15.

2.1.3.1 Heater Wrap

Figure 16:
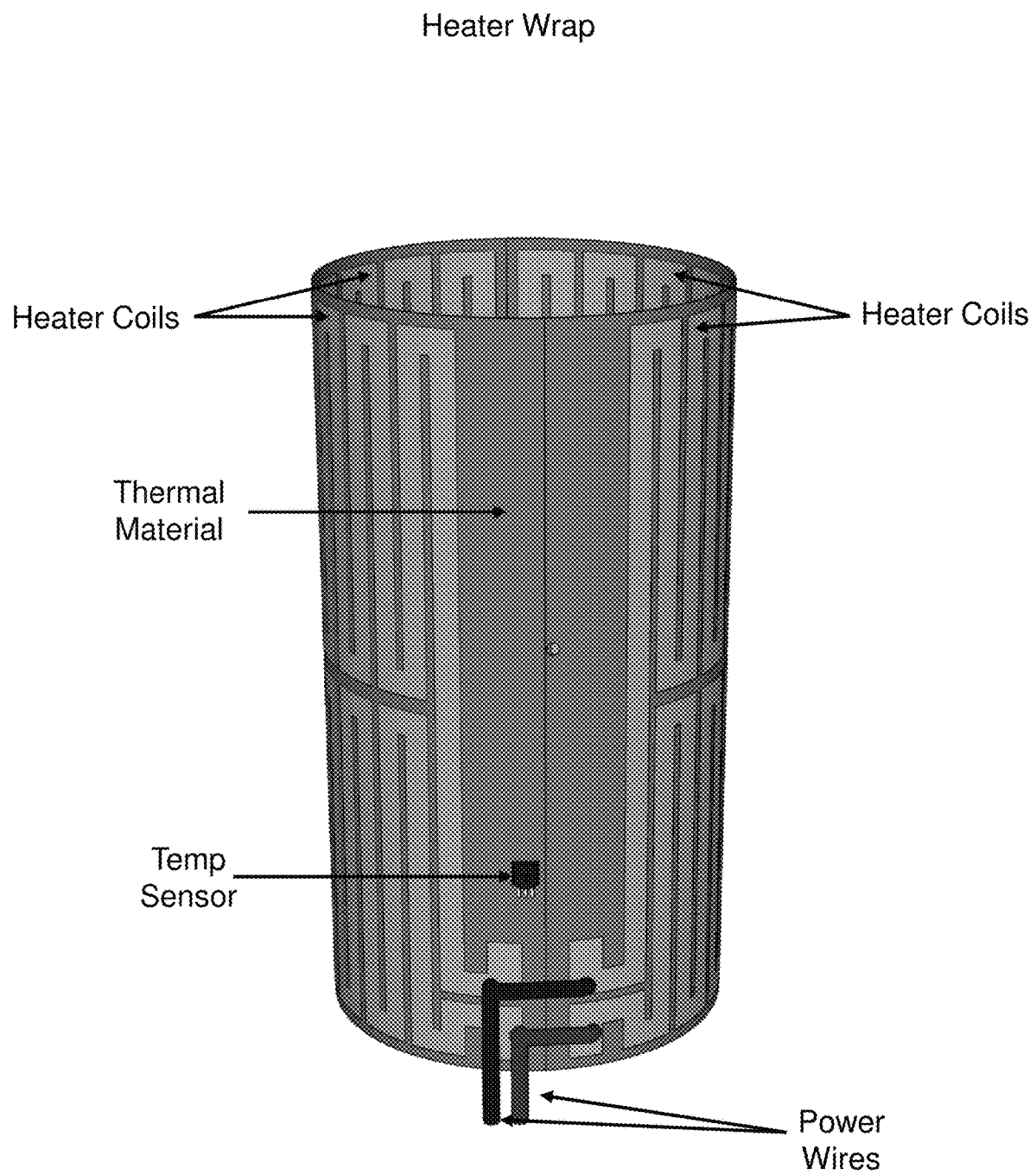
FIG. 16 is an exemplary diagram of an ECU heater wrap that may be used to implement aspects of certain embodiments of the present invention.

The outside layer of an ECU is the heater wrap, shown in FIG. 15 and in more detail in FIG. 16. A heater wrap may be used to quickly apply heat to the contents of the payload chamber. The heater wrap consists of resistive heater coils printed on a thermally conductive material. The material may or may not be flexible. The heater coils may be printed on just the outside or on both the inside and outside of the wrap. An alternative to resistive heating may be induction heating. Different types of heating methods may be used without limitation. The energy used for the heating may be AC or DC, low voltage or high voltage, or modulated DC (e.g. analog variable voltage, PAM, PWM, etc.)

The wrap itself may be one or more sections (two sections are shown in the embodiment of FIG. 16) that are then adhered to the heat conducting shell. Adhesion may be through any method that meets the requirements of the application, whether via glue, tape, static, friction, or other adhering method. The wrap may be positioned next to the heat conducting shell instead of being adhered to it.

When power is applied to the resistive coils, they generate heat energy which is passed through the heat conducting shell and into the payload chamber. The amount of heat and rate of change of temperature, and thus the rate of heat transfer may be controlled by the microcontroller to be optimized for the particular type of payload contained in the payload chamber.

A temperature sensor may be mounted to the outside of the heat wrap to measure the temperature of the heat conducting shell so that the temperature gradient between the heat conducting shell and the temperature sensor inside the payload chamber may be determined. The heat conducting shell sensor also provides feedback to the microcontroller so that the amount of energy sent to the heater coils may be properly controlled. They may be controlled for user safety (e.g. over-heating protection) as well as to maintain proper operation. The temperature sensor may also be mounted directly to the heat conducting shell with no loss in functionality.

2.1.3.2 Heat Conducting Shell

Figure 17:
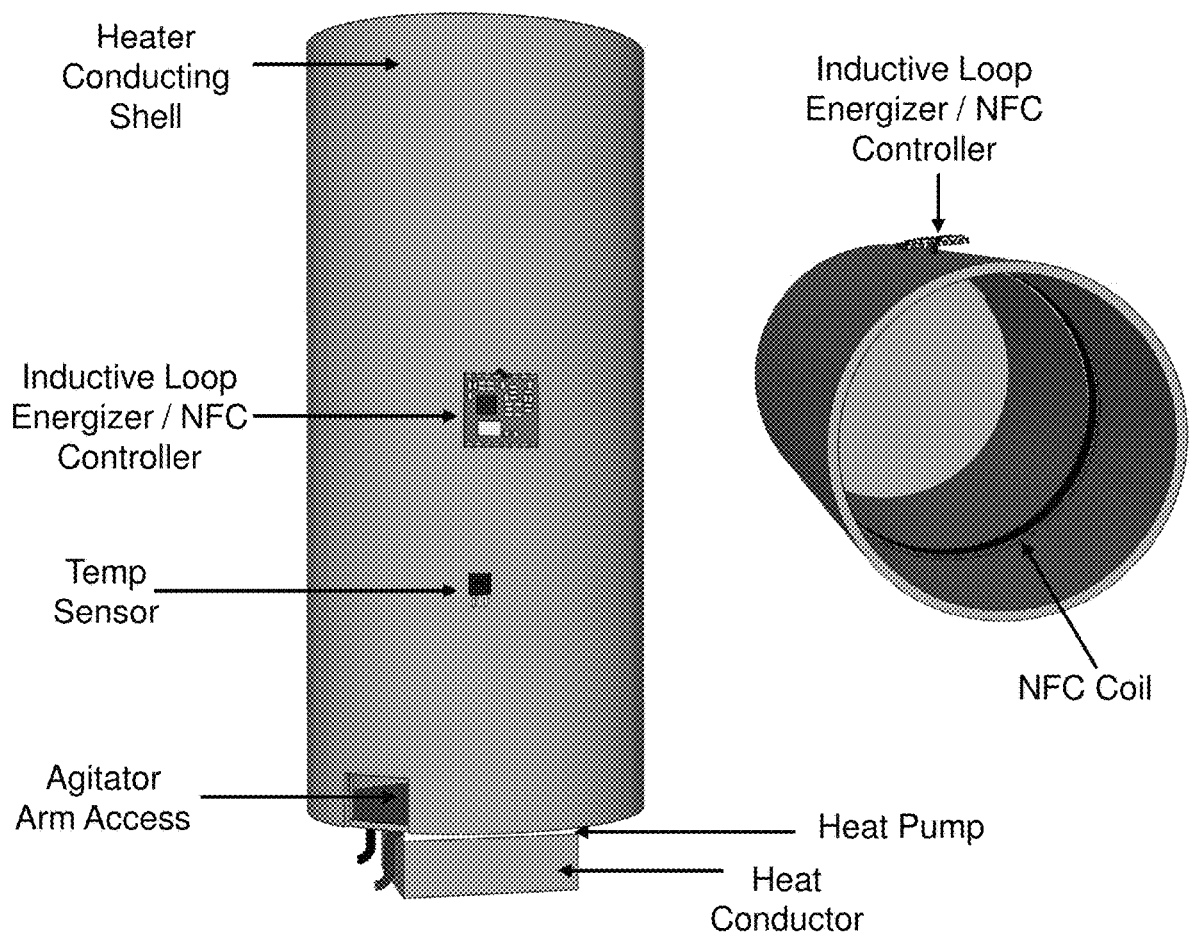
FIG. 17 is an exemplary diagram of the ECU heat conducting shell that may be used to implement aspects of certain embodiments of the present invention.

FIG. 17 shows an embodiment of the heat conducting shell. The heat conducting shell transfers heat generated by the heater wrap to the payload chamber which may fit inside it. The shell may be manufactured as one or more sections and may be comprised of a low thermal resistance material, such as copper, aluminum, diamond, etc. The shell may also be manufactured as one or more sections and may be comprised of a transparent material, such as, plastic, glass, etc.

The heat conducting shell may also be used to draw heat away from the payload when the payload requires cooling. In this mode the heater wrap may be turned off. The heat pump may pump heat away from the payload and through the heat conductor block to the heat exchanger where the heat is then either reused by one of the other ECUs or transferred to the environment. This reuse of thermal energy may prolong battery life and improve overall power efficiency. The heat pump, which is located at the bottom of the shell in the embodiment of FIG. 17, may be located anywhere on the heat conducting shell without impacting performance or functionality. The heat pump may also be used to assist in warming the payload or maintaining warmth in the payload. It should be noted that there may be more than one heat pump. They may be stacked together or placed on multiple locations around the heat conducting shell.

An NFC controller, which may be powered by the enclosure's power supply, may be attached to the heat conducting shell for energizing an NFC coil which may be placed on the interior of the heat conducting shell. This NFC coil may be used to transfer energy to be picked up by the thermal transfer cup's NFC coil (FIG. 4) and to receive a signal from the cup's sensors. Other mechanisms (e.g. Bluetooth, Zigbee, BLE, etc.) aside from NFC may be used to accomplish the same functionality as that performed using the NFC approach.

2.1.3.3 Heat Pump

The heat pump utilized by the ECUs may be a thermoelectric device such as a Peltier heat pump. A Peltier heat pump is a solid-state active heat pump which transfers heat from one side of the device to the other, with consumption of electrical energy, depending on the direction of the current. It uses the Peltier effect to create a heat flux between the junction of two different types of materials. One or more heat pumps may be stacked together to improve energy efficiency as well as to increase the rate of temperature change.

Figure 18:
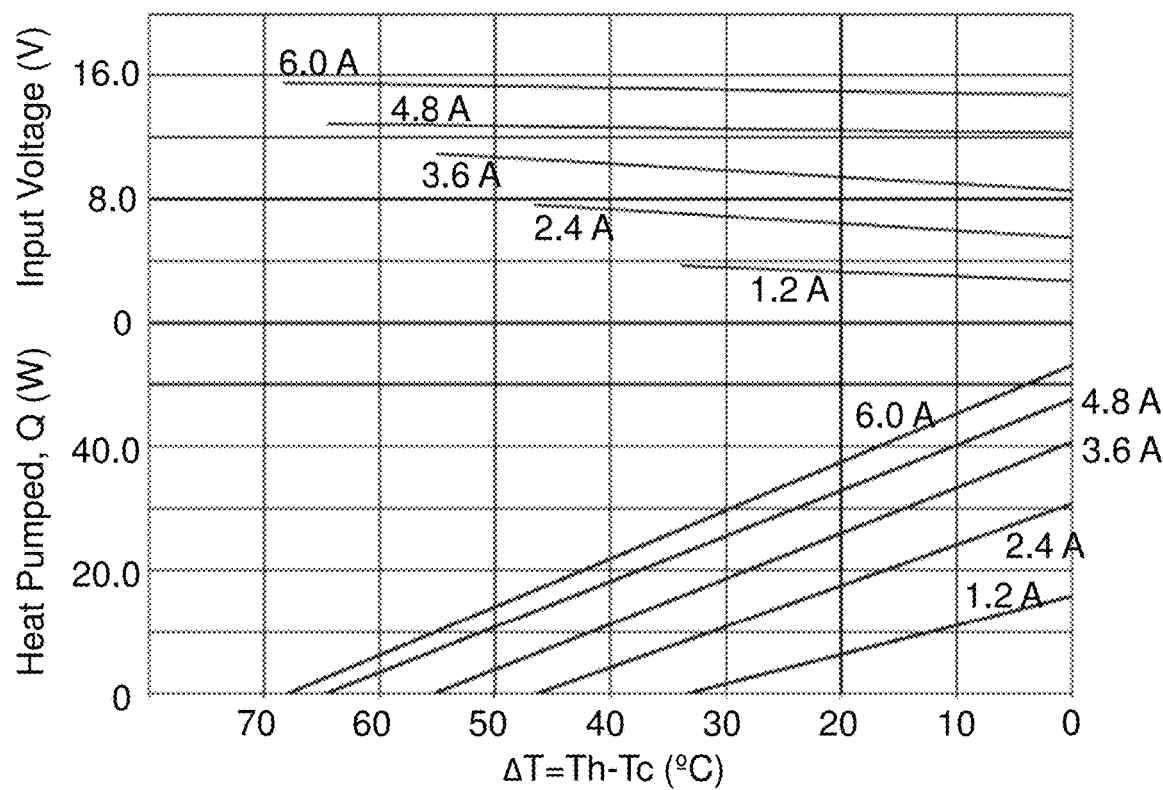
FIG. 18 is an exemplary graph of dT_C vs. HeatPump_W that may be used to implement aspects of certain embodiments of the present invention.

An example heat pump that may be used is the CP60440 from CUI, Inc. The performance for the CP60440 in terms of $dT\_C$ (temperature difference between first-side and second-side of a Peltier module) vs. HeatPump_W ($Q\_W$ is the amount of heat energy pumped from the first-side to the second-side of a Peltier module), where the $DT\_C$ vs. Input Voltage is shown in FIG. 18.

These graphs characterize the Peltier modules to determine the heat pumping performance of the heat pump when operating conditions are given.

The following two examples show heat pumping performance is better when $dT\_C$ is smaller.

Pin_W=~57.6, dT_C=10, Q_W=40

Pin_W=~57.6, dT_C=15, Q_W=36

When Pin_W (wattage consumed by Peltier based on input voltage and current) is held constant, for example at ~57 W, an increase of 5 C in temperature differential results in a heat transfer flow of 4 W less being pumped by the heat pump. Another way to think about it is at dT_C=10, the amount of input power applied to the heat pump yields better pumping action and may thus save more energy, since for a given amount of desired heat transfer, the pump may be run for a shorter time period and hence less energy would be required. It therefore, may be advantageous to create a configuration where the dT_C is kept as small as practical.

Figure 19:
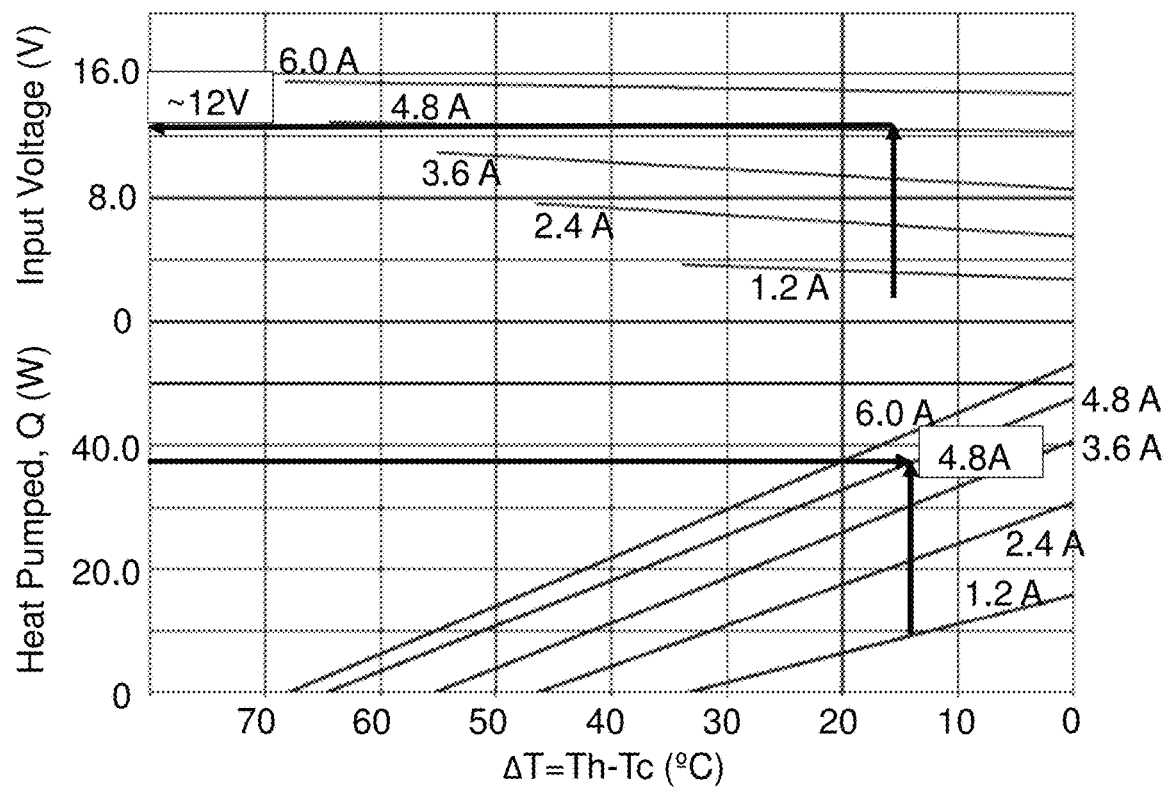
FIG. 19 is an exemplary graph for dT_C=15, W=36 that may be used to implement aspects of certain embodiments of the present invention.

FIG. 19 provides an example of how to use the table/graph provided by a manufacturer. The following steps are followed:

1. Determine Current_A when operating conditions are dT_C=15 and Q_W=36.

a. Current_A=4.8 A (shown in lower half of graph in green)

2. Determine InputVoltage_V when operating conditions are dT_C=15 and Current_A=4.8 A.

a. InputVoltage_V=~12V (shown in upper half off graph in orange)

3. Calculate InputPower_W as InputVoltage_V*InputCurrent_A a. InputPower_W=~57.6 W 4. Calculate Efficiency_% as HeatPumpedQ_W÷InputPower_W a. Efficiency_%=~63%

Following the same approach, one can see that at a dT_C of 10, the Efficiency_% would be approximately 69%.

Below the heat pump is a block of heat conducting material. It may be used to adjust the height of the ECU within the enclosure and may also be used to interface the heat pump to the heat exchanger. The block may be any shape and size, though the embodiment of the figures shows it to be the same surface area as the heat pump. The block may be made of any low thermal resistance material with the desired properties.

2.2 Alarms and Alerts

The controlled environment system, and also Cloud, are capable of generating (e.g. screen indicator, alerts to remote devices, etc.) alarms and alerts based on detected conditions as well as predictions of future conditions. The alarm and alert mechanisms will inform the user about various scenarios including but not limited to the following examples:
 a) ECU temperature control failure
 b) Initial payload temperature too high or low
 c) System Reset/Power Failure
 d) The battery level is running low
 e) Payload temperature target achieved
 f) Payload ready but in chamber for too long
 g) The payload chamber has been tampered with
 h) The payload chamber has been left open or is unsealed
 i) The payload chamber has fallen over
 j) Shock/vibration alarm
 k) Upper or lower temperature limit alarms
 l) Current conditions are prime for payload deterioration
 m) Predictive alerts, such as, days before payload spoils, time before payload is too dry, etc.

Some of these alarms may be dependent on a motion sensor, such as a gravitational sensor, a MEMS sensor, an accelerometer, or a combination of these or similar type sensors.

A chemical sensor may also be implemented to determine the presence of and/or amount of mold in the environment or the number of bacteria in the environment. An alarm may be dependent on this sensor as well as other sensors.

There may be an odor sensor (detector) on the outside of the Controlled Environment System. This may detect an odor that exceeds a predetermined threshold. If this occurs, an alarm may be generated for the user.

There may also be an odor sensor (detector) on the inside of the Controlled Environment System. This may detect an odor that exceeds a predetermined threshold. If this occurs an alarm may be generated for the user.

There may be a light sensor that measures the duration and/or intensity level of light that the payload is subject too.

At least one camera may be coupled to the Controlled Environment System. The camera may be remotely accessible for control and data download. Pictures or video may be taken of the inside of the payload chamber as well as the outside of the payload chamber, as well as the external environment such that the camera may be used as a baby monitor. The camera may also be used to track milk usage per feeding. The video and pictures taken may be continually taken or may be performed when the user requests as well as when an alarm is generated or at a predetermined time period. This data may be fed into a database for analysis or may be routed to a user or a set of application users.

Spectral/chemical analysis of the payload and/or payload chamber environment may be performed. Spectroscopy is a powerful technique for recognizing and characterizing physical materials in various phases, including but not limited to, solid, liquid, gas, or plasma, and may be light emitting or light absorbing. Such analysis may be performed using Texas Instruments (TI) DLP Near-Infrared (NIR) technology. Near-Infrared (NIR) products may be optimized for 700 nm to 2500 nm wavelengths and may deliver high SNR. Spectral/chemical analysis may then enable the ECU to determine specific chemical or nutrient levels and determine how best to control the environment to obtain the desired results.

3 Environmental Control Unit Functionality

In certain embodiments, an ECU may be operated in many different modes, depending on the requirements of each particular implementation. Some of the possible modes may be Idle mode, Economy mode, and Turbo mode. Sub-modes of Economy and Turbo modes may be Heating, Cooling, Humidification, and Dehumidification.

In Idle mode, housekeeping functions may be performed by the enclosure and ECU, but the environment of a payload chamber in Idle may not be actively treated. In Economy mode, the environment of a payload chamber may be controlled, but at a slower rate, so as to conserve power. In Turbo mode, the environment of the payload chamber may be controlled in a manner so that the programmed environmental conditions may be attained more quickly. A user may transition an ECU between modes or the controller may also cause a transition between modes.

3.1 Idle Mode

If the environment within an ECU is at the desired state, no adjustments necessary, then that unit may be placed in Idle mode. During Idle mode, the heater wrap and the heat pump may be off. The associated agitator may or may not be in use, or may be used intermittently during Idle so as to keep the payload temperature evenly distributed. This may cause the payload's temperature to stay relatively the same unless conditions change, such as outside influencers of the environment or the payload state experienced a change.

If an event that may impact functionality occurs (e.g. payload chamber removed, payload chamber opened, ECU fault, etc.), then the unit may be placed into the Idle mode and an alarm or notification generated to the user. It is important to remember that the ECUs may be treated independently such that any conditions in one may not impact conditions in another.

3.2 Economy Mode

In Economy mode, the environment within an ECU may be controlled in an energy conserving manner. This may mean that it takes longer for a payload to reach its target temperature. It may also mean that a payload has reached its target temperature or state and that only the energy to maintain that state is required.

While an ECU is in Economy mode, all aspects of its environmental control (i.e. heater wrap, temperature sensors, heat pump, heat exchanger fans, etc.) may be utilized to maintain or change the environment, but they may be utilized in a slow, energy conserving manner. As an example, both the heat pump and heater coils may be utilized in a low energy configuration to reach a set target temperature, but once the temperature is attained, only the heat pump may be used to maintain the temperature.

If an event that may impact functionality occurs, then the particular ECU may be transitioned to the Idle mode and an alarm or notification generated to the user.

3.3 Turbo Mode

In Turbo mode, the environment within an ECU may be controlled in a non-energy conserving manner. This may mean that a payload is regulated to its target temperature as quickly as possible given the constraints of the payload type (so as not to damage the nutrient content or other aspects of the payload). Once the target temperature is attained, the ECU may be transitioned to Idle or Economy mode. All aspects of an ECU's environmental control (i.e. heater wrap, temperature sensors, heat pump, heat exchanger fans, etc.) may be utilized while in Turbo mode. An example of a possible Turbo mode application is sterilization of baby bottle components. Water may be added to the payload chamber with the components placed inside. Rapid heating to cause steaming and the spread of high temperatures within the payload chamber may result in full sterilization of all the items within the payload chamber.

Another example of possible Turbo mode usage may be for rapid cooling and cooling to the point of freezing. This may be used for preparing breast milk for long term storage so as to reduce the risk of spoilage.

If an event that may impact functionality occurs, then the particular ECU may be transitioned to the Idle mode and an alarm or notification generated to the user.

3.4 Environment Control

3.4.1 Heating

Heating may be performed by energizing the heater wrap alone, the heat pump alone, or in combination with the heat pump. The heat pump may draw heat from the heat exchanger and direct it to the heat conducting shell and the payload chamber. One or more fans, depending on the conditions of the other ECUs, may or may not be operated.

While heating, the agitator assembly may be active to evenly distribute the thermal energy through the payload. The temperature of the payload may be monitored by the enclosure control board and when the payload reaches the desired temperature, the ECU may be placed into Idle mode and a notification generated.

3.4.2 Cooling

While cooling, an ECU's heat wrap may be turned off and the heat pump used to pump thermal energy away from the payload. The heat exchanger fans may or may not be active, possibly depending on the temperature differential from the inlet to exhaust and also the temperature differential between the heat pump and heat exchanger. The fans may be run at the speed calculated by the enclosure controller.

While cooling, the agitator assembly may be active to evenly distribute the thermal energy through the payload. The temperature of the payload may be monitored by the enclosure control board and when the payload reaches the desired temperature, the ECU may be placed into Idle mode and a notification may be generated.

4 Control and Calibration Algorithms

Sensors are placed at various locations within the controlled environment system to provide information to the various control loops such that environmental conditions may be set, adjusted, and monitored. A controlled environment system, has sensors (FIG. 15) to monitor heat conducting shell temperature and payload chamber conditions (FIG. 4) as well as to control and monitor the ECU's operation. The conducting shell temperature sensor combined with the heat exchanger temperature allows the coefficient of performance of the heat pump to be properly controlled and monitored.

Sensors located at the fan inlet and exhaust (FIG. 8) measure the current ambient temperature as well as the heat exchanger temperature. Using these sensors, the current enclosure conditions can be ascertained as well as the impact of treating the environment within the ECUs.

In addition to sensors for monitoring the air path and ECU conditions, the microcontroller board may have additional sensors for detecting controlled environment system movement and position, among other information.

Remote sensors, connected either wired or wirelessly to an ECU, may be placed into one or more locations within the payload chamber for more accurate readings of payload conditions when the enclosed space is large enough to warrant it or the density of the payload area is high enough. Placing remote sensors may allow the control loops in the main unit to get a better feedback on how temperature is spreading throughout the payload chamber by using the temperature data that the remote sensor modules may provide.

The following sections will go into detail on some of the control and calibration algorithms performed within the controlled environment system.

Figure 20:
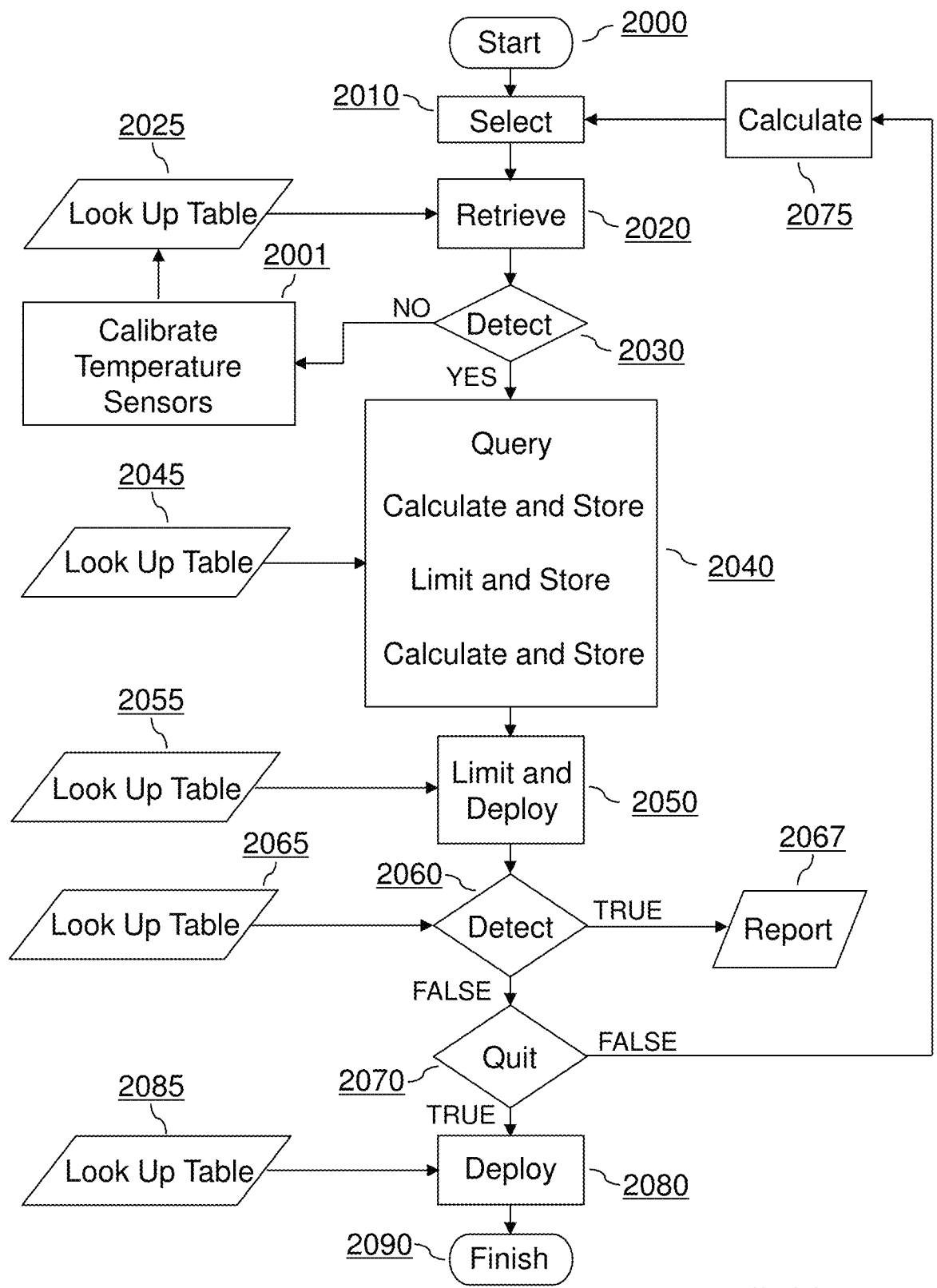
FIG. 20 is an exemplary diagram of a heat pump control algorithm that may be used to implement aspects of certain embodiments of the present invention.

4.1 Heat Pump—Control Algorithm (FIG. 20)

TABLE 1

Heat Pump Control Mode - Block Descriptions

| Reference Designator | Component Type | Description |
| --- | --- | --- |
| 2000: Start | Terminal | Start point for control algorithm is entered after User initiates the control. This is assumed to occur once User selects the item to be stored and the atmospheric condition is determined. i = 0 |
| 2010: Select | Process | The product design may include zero, one or more than one heat-pump-channels (HPC). This process selects one of the HPCs to be the current unit-under-control (UUC). The UUC is indicated by iteration variable "i". UUC[i] |
| 2020: Retrieve | Process | Retrieve the contents of the calibration look-up table for UUC. TS Cal Factors for UUC[i] |
| 2025: Look Up Table | Input/Output | Look-up table contains calibration coefficients for the UUC. TS Cal Factors[i] |
| 2030: Detect | Decision | Detect if calibration coefficients exist for UUC. If no coefficients exist, enter the Calibration Algorithm. If coefficients exist, then continue. Calibrated? |

TABLE 1-continued

Heat Pump Control Mode - Block Descriptions

Figure 21:
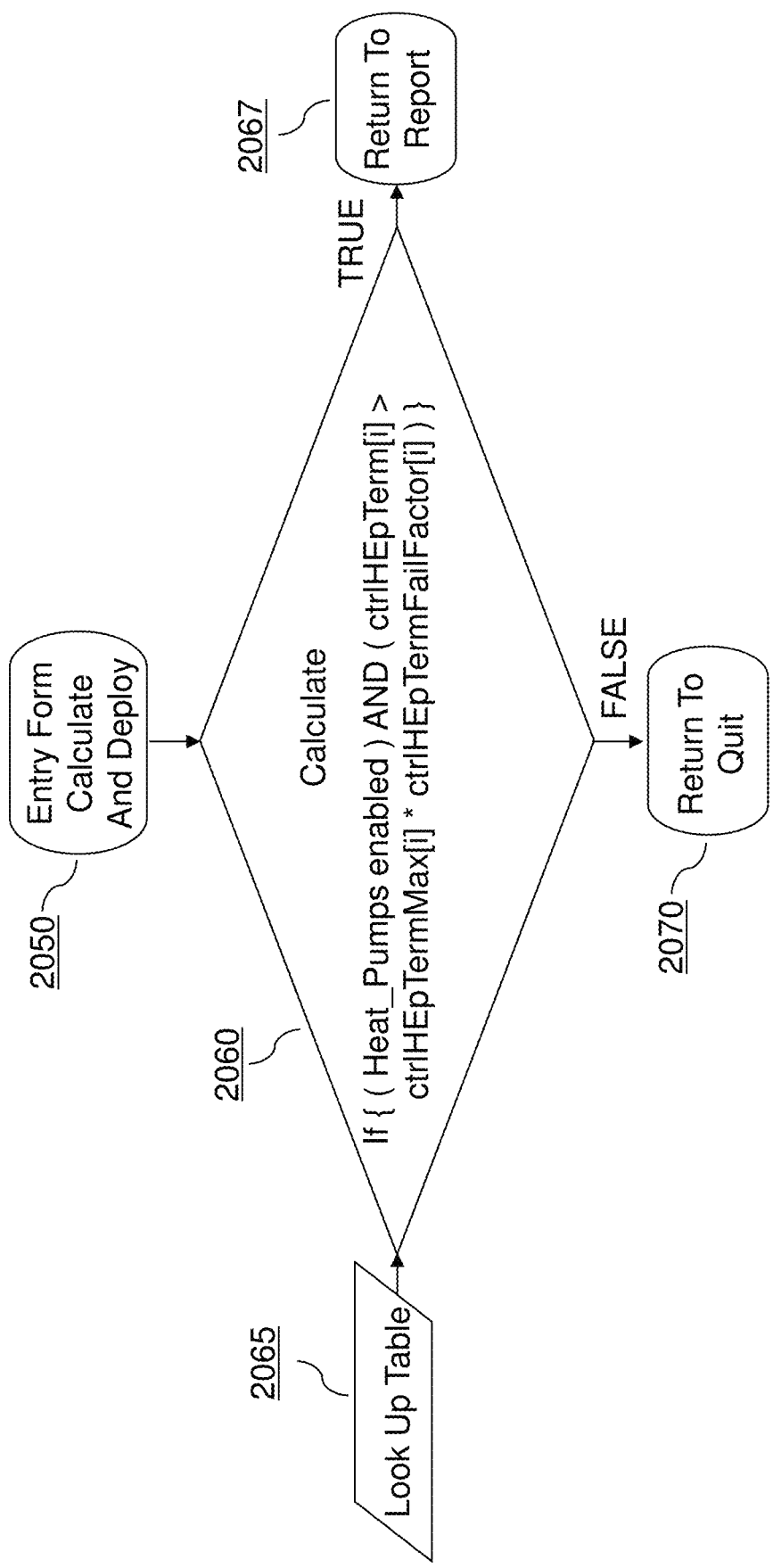
FIG. 21 is an exemplary diagram of heat pump failure detection that may be used to implement aspects of certain embodiments of the present invention.

| Reference Designator | Component Type | Description |
|---|---|---|
| 2040: Query | Process | Query from the heat exchanger temperature sensor (TS_HEx) and temperature sensor of the item being stored (TS_item). Apply calibrations. TS_HEx[i] and TS_item[i] Calculate and store the error term (errTerm) as being the difference between the target set point (TS_itemSP) and the temperature of the item being stored (TS_item). errTerm[i] = (TS_itemSP[i] − TS_item[i]) Calculate and store the limiter term (limTerm) as being the difference between the temperature of the item being stored (TS_item) and the temperature of the heat exchanger (TS_HEx). limTerm[i] = (TS_HEx[i] − TS_item[i]) Depending upon if limiter term exceeds target limits, limit error term. If (limTerm[i] > TS_dTarget[i]) then errTerm[i] = errTerm[i]/limTermFactor[i] else errTerm[i] = errTerm[i] Calculate and store the control term (ctrlTerm) using control-loop and PID coefficients along with the error term. ctrlHEpTerm[i] = PID ( errTerm[i] ) |
| 2045: Look Up Table | Input/Output | Look-up table contains temperature target and feed-back control-loop coefficients (PID). TS_itemSetPoint[i] TS_dTarget[i] limTermFactor[i] PID Terms |
| 2050: Limit and Deploy | Process | Limit the control term to not exceed functional limits, ctrlHEpTermMax. Deploy limited ctrlTerm to Power Management Unit. ctrlHEpTerm[i] = min( ctrlHEpTerm[i], ctrlHEpTermMax[i] ) |
| 2055: Look Up Table | Input/Output | Look-up table contains the maximum setting allowed for the heat pump, ctrlHEpTermMax. ctrlHEpTermMax[i] |
| 2060: Detect (see FIG. 21) | Decision | Test calculated ctrlHEpTerm and limited ctrlHEpTerm to determine if the control loop is failing to converge, suggesting that heat pump is failing to provide sufficient heat flow through the heat exchanger. If { ( Heat_Pumps enabled) AND . ( ctrlHEpTerm[i] > ctrlHEpTermMax[i] * ctrlHEpTermFailFactor[i] ) AND. } UUC[i] failure? |
| 2065: Look Up Table | Input/Output | Look-up table contains the maximum setting allowed for the heat pump, ctrlHEpTermMax and factor for considering when failure has occurred, ctrlHEpTermFailFactor. ctrlHEpTermMax[i] ctrlHEpTermFailFactor[i] |
| 2067: Report | Input/Output | Report if UUC[i] failed |
| 2070: Quit | Decision | If this control algorithm is not issued a Quit from a higher process, then continue control algorithm, with next UUC. If control algorithm is issued a Quit, then discontinue control algorithm. Ctrl Algo? |
| 2075: Calculate | Process | The product design may include zero, one or more than one heat-pump-channels (HPC). This process calculates new value for iteration variable "i". i = mod( i + 1, numUUCMax ) |
| 2080: Deploy | Process | When discontinuing the control algorithm, deploy ctrlHEpTermMin to Power Management Unit, disabling all heat pumps. ctrlHEpTerm[i] = ctrlHEpTermMin[i] |
| 2085: Look Up Table | Input/Output | Look-up table contains the minimum setting allowed for the heat pump, ctrlHEpTermMin. ctrlHEpTermMin[i] |
| 2090: Finish | Terminal | Finish point for control algorithm is entered after User terminates the control. This is assumed to occur when User sets the product to Stand-by mode. |

TABLE 2

Heat Pump Control Mode - Parameter List

| Name | Symbol | Description | Units |
|---|---|---|---|
| 2001: Temperature Sensor Calibration Factor | TS Cal Factors[i] | Calibration factor for temperature and humidity sensors. | Celsius |
| Target set point temperature for ECU | TS_itemSP[i] | Target temperature for the item being stored. Temperature is selected depending upon the item being stored. This temperature is the control-loop set point. | Celsius |

TABLE 2-continued

Heat Pump Control Mode - Parameter List

| Name | Symbol | Description | Units |
|---|---|---|---|
| Target delta temperature | TS_dTarget[i] | Target temperature differential between the heat exchanger and the item being stored. This differential temperature is a limit applied to the control-loop error term. | Celsius |
| Proportional, Integral, Derivative Coefficients | PID Terms[i] | Control-loop coefficients for configuration loop stability and settling characteristics. | Unitless |
| Heat Pump Control Term | ctrlHEpTerm[i] | The control setting for the heat pump, HEp[i]. | Volts |
| Heat Pump Control Term - Max | ctrlHEpTermMax[i] | The maximum operational control setting allowed for the heat pump, HEp[i]. | Volts |
| Heat Pump Control Term Fail Factor | ctrlHEpTermFailFactor[i] | The multiplication factor used to determine when UUC[i] has failed. | Unitless |
| Heat Pump Control Term - Min | ctrlHEpTermMin[i] | The minimum operational control setting allowed for the heat pump, HEp[i]. | Volts |

4.2 Control Loop Coefficients

Figure 22:
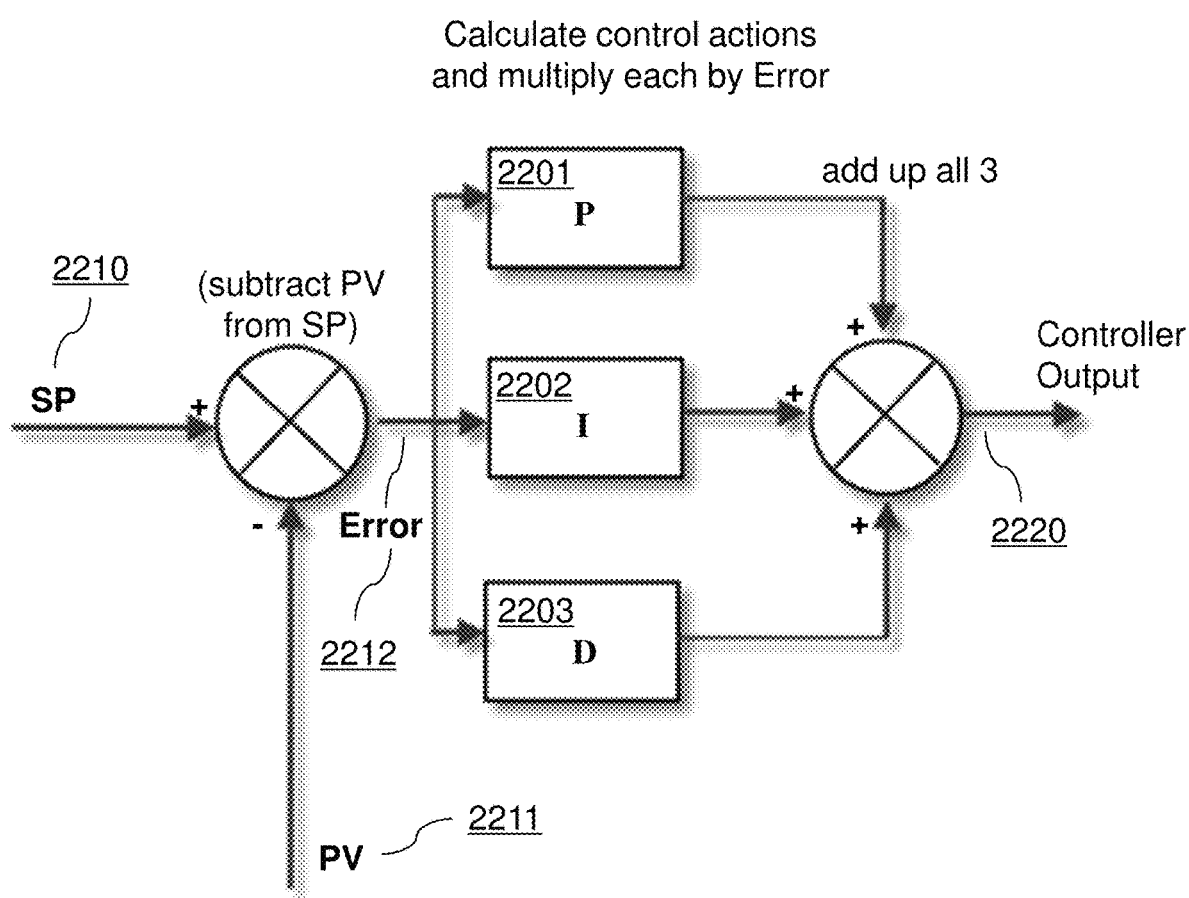
FIG. 22 is an exemplary diagram of a proportional, integral, derivative control loop that may be used to implement aspects of certain embodiments of the present invention.

In certain embodiments, precisely managing the temperature/humidity of the payload chamber and differential temperature may be accomplished by the use of a Proportional, Integral, and Derivative (PID) control loop, shown in FIG. 22.

Managing the payload chamber temperature may be by use of a feedback control loop. The process variable is the measured ambient temperature of the payload chamber. The process set point is a temperature which may be selected depending upon the payload item. The process controller output may either be the supply voltage to the heat pump and heater wrap when the task is to increase the temperature or may be the supply voltage to the fan and heat pump when the task is to decrease the temperature. When the control loop has converged, the three goals of efficacy, efficiency, and simplicity may have been accomplished.

Table 3 cross-references parameters used in the flow diagrams and the simplified diagram of the control loop, shown in FIG. 22

TABLE 3

Control Loop Diagram to Flow Diagram Cross Reference

| Signal | Flow Diagram | Control Loop Diagram |
|---|---|---|
| 2210: Set Point | TS_itemSP[ ] | SP |
| 2211: Process Variable | TS_item[ ] | PV |
| 2212: Error Term | errTerm[ ] | Error |
| 2201: Proportional Term | P | P |
| 2202: Integral Term | I | I |
| 2203: Derivative Term | D | D |
| 2220: Controller | ctrlHEpTerm[ ] | Controller Output |

4.3 Calibration Mode

In Calibration Mode, algorithms are exercised to measure temperature characteristics of various elements. With the measurements, calibration tables are produced which improve the accuracy of the elements which in turn improve the efficacy and efficiency of the design.

4.3.1 Calibration Mode—Heat Exchanger

In Calibration Mode, the control software configures the hardware elements to a pre-determined state and measures differential imbalances of the temperature sensors.

With the use of calibration and differential measurements during Operational Mode, low cost temperature sensors with their expected variation in temperature reporting accuracy due to production process variation may be used.

Figure 23:
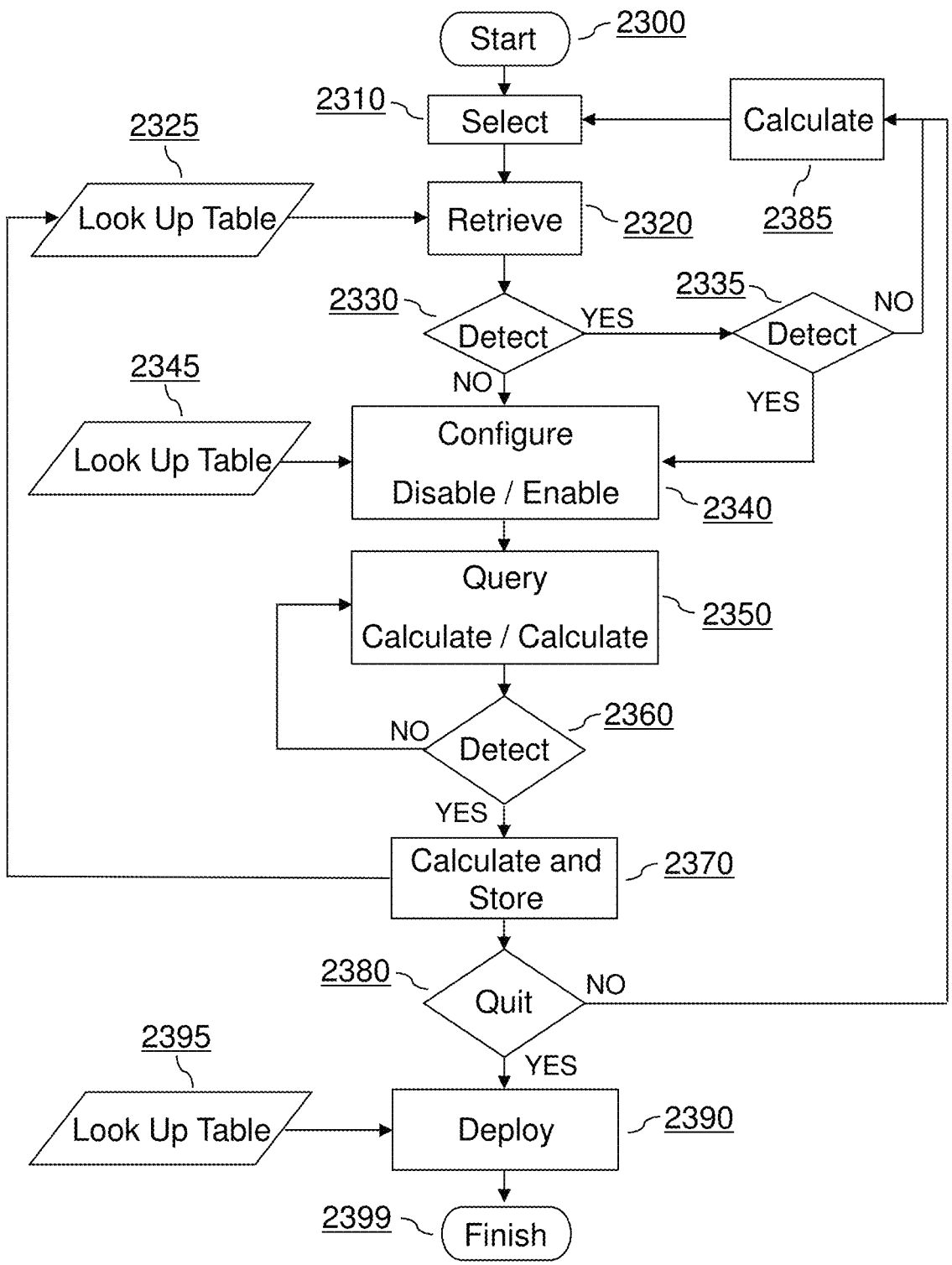
FIG. 23 is an exemplary diagram of a heat pump calibration algorithm that may be used to implement aspects of certain embodiments of the present invention.

Calibration of the heat exchanger sub-assembly is accomplished by calibration of the ECU subassembly. The algorithm for calibration for the heat pumps is shown in FIG. 23 and explained in Table 4 and Table 5.

4.3.1.1 Calibration Mode: Flowchart—Heat Exchanger (FIG. 23)

TABLE 4

Calibration Mode: Heat Exchanger - Block Descriptions

| Reference Designator | Component Type | Description |
|---|---|---|
| 2300: Start | Terminal | Start point for calibration algorithm is entered when control algorithm detects that there are no existing calibration coefficients. i = 0 |
| 2310: Select | Process | The product design may include zero, one or more than one heat-pumped-channels (HPCs). This process selects one of the HPCs to be the unit-under-control (UUC). The UUC is identified with iteration variable "i". UUC[i] |

TABLE 4-continued

Calibration Mode: Heat Exchanger - Block Descriptions

| Reference Designator | Component Type | Description |
| --- | --- | --- |
| 2320: Retrieve | Process | Retrieve the contents of the calibration lookup table for the UUC. <br> TS Cal Factors for UUC[i] |
| 2325: Look Up Table | Input/Output | Lookup table contains calibration coefficients for the UUC. <br> TS Cal Factors[i] |
| 2330: Detect | Decision | Detect if calibration coefficients exist for UUC. If no coefficients exist, enter the Calibration Algorithm. If coefficients exist, then continue. <br> Calibrated? |
| 2335: Detect | Decision | Detected that calibration coefficients exist, yet recalibration is desired. <br> Forced ReCal? |
| 2340: Configure | Process | Configure the hardware elements for calibration mode. <br> Disable All H Ep[ ] <br> ctrlHEpTerm = ctrlHEpTermMin[k] <br> Ensure that all heat pumps are disabled as the calibration algorithm relies on the heat exchanger and the payload chamber to be at the same temperature. <br> Enable FAN[i] at flow rate determined by maximum flow rate and a scaling factor. <br> Enable FAN[i] <br> ctrlFANTerm = ctrlFANTermMax[i] * ctrlFANTermCalFactor[i] |
| 2345: Look Up Table | Input/Output | Lookup table contains the maximum setting allowed for the UUC. <br> ctrlHEpTermMin[k] <br> ctrlFANTermMax[i] <br> ctrlFANTermCalFactor[ ] |
| 2350: Calculate and Deploy | Process | Query from the heat exchanger temperature sensor (TS_HEx[ ]) and temperature sensor of the item being stored (TS_item[ ]) the current temperatures. <br> TS_HEx[i] and TS_atm[i] <br> Calculate and store the average and standard deviation statistics from heat exchanger and item being stored temperature sensor queries. <br> AVE and STDEV of TS_HEx[i] <br> AVE and STDEV of TS_atm[i] |
| 2360: Detect | Decision | Compare the standard deviation of the sensor queries. When standard deviations are near equal, then can assume that heat exchanger and payload chamber temperatures have settled. <br> Does STDEV(TS_HEx[i]) = STDEV(TS_atm[i]) |
| 2370: Calculate and Store | Decision | Calculate calibration coefficients and store in Lookup Table. <br> calFactor[i] = AVE(TS_HEx[i]) − AVE(TS_atm[i]) |
| 2380: Quit | Decision | Determine if all HPCs have been calibrated. <br> All TSs Calibrated? |
| 2385: Calculate | Process | Calculate <br> i = mod( i + 1, numUUCMax ) |
| 2390: Deploy | Process | When discontinuing the calibration algorithm, deploy ctrlTermMin[ ] to Power Management Unit, disabling all heat pumps. <br> ctrlFanTerm[i] = ctrlFanTermMin[i] |
| 2395: Look Up Table | Input/Output | Lookup table contains the minimum setting allowed for the heat pump. <br> ctrlFanTermMin[i] |
| 2399: Finish | Terminal | Finish point for calibration algorithm is entered after all temperature sensors associated with HPCs have been calibrated and FANs have been disabled. |

TABLE 5

Calibration Mode: Dehumidifier - Parameter List

| Name | Symbol | Description | Units |
| --- | --- | --- | --- |
| Temperature Sensor Calibration Factors | TS Cal Factors[i] | Calibration factor for temperature sensor located at outlet of forced-air heat exchanger, TS_out[i]. This calibration factor is relative to TS_in[i]. | Celsius |
| Heat Pump Control Term - Min | ctrlHEpTermMin[i] | The minimum operational control setting allowed for the heat pump[i]. | Volts |
| FAN Control Term - Max | ctrlFANTermMax[i] | The maximum operational control setting allowed for the FAN[i]. | Volts |
| FAN Control Term Calibration Factor | ctrlFANTermCalFactor[i] | The multiplication factor used to set FAN control during calibration. | Unitless |
| FAN Control Term - Min | ctrlFANTermMin[i] | The minimum operational control setting allowed for the FAN[i]. | Volts |

4.4 Forced-Air Heat Exchanger Control Algorithm for Low Observability Applications A control algorithm is presented for a forced-air heat exchanger that ensures effective and efficient heat energy transfer while obscuring acoustic signatures.

When developing forced-air heat exchanger designs for low observability applications, three goals may be identified. The first goal is that the design must be effective. A design which does not accomplish its task has no need for efficiency nor low observability as the design will not be fielded.

The second goal is that the design must be efficient. The desire is for the design to consume only as much energy as is required to complete the task. Inefficiencies result in excess energy that exit the design, increasing the opportunity for observation.

The third goal is that the design must obscure energy escaping from the design. Observation is more likely when the escaping energy is significantly different from those of its surroundings. Obscuration techniques include distributing energy over larger physical areas or over longer time periods and directing the energy away from the observer. These techniques serve to minimize the energy density and thus likelihood of observation.

Figure 24:
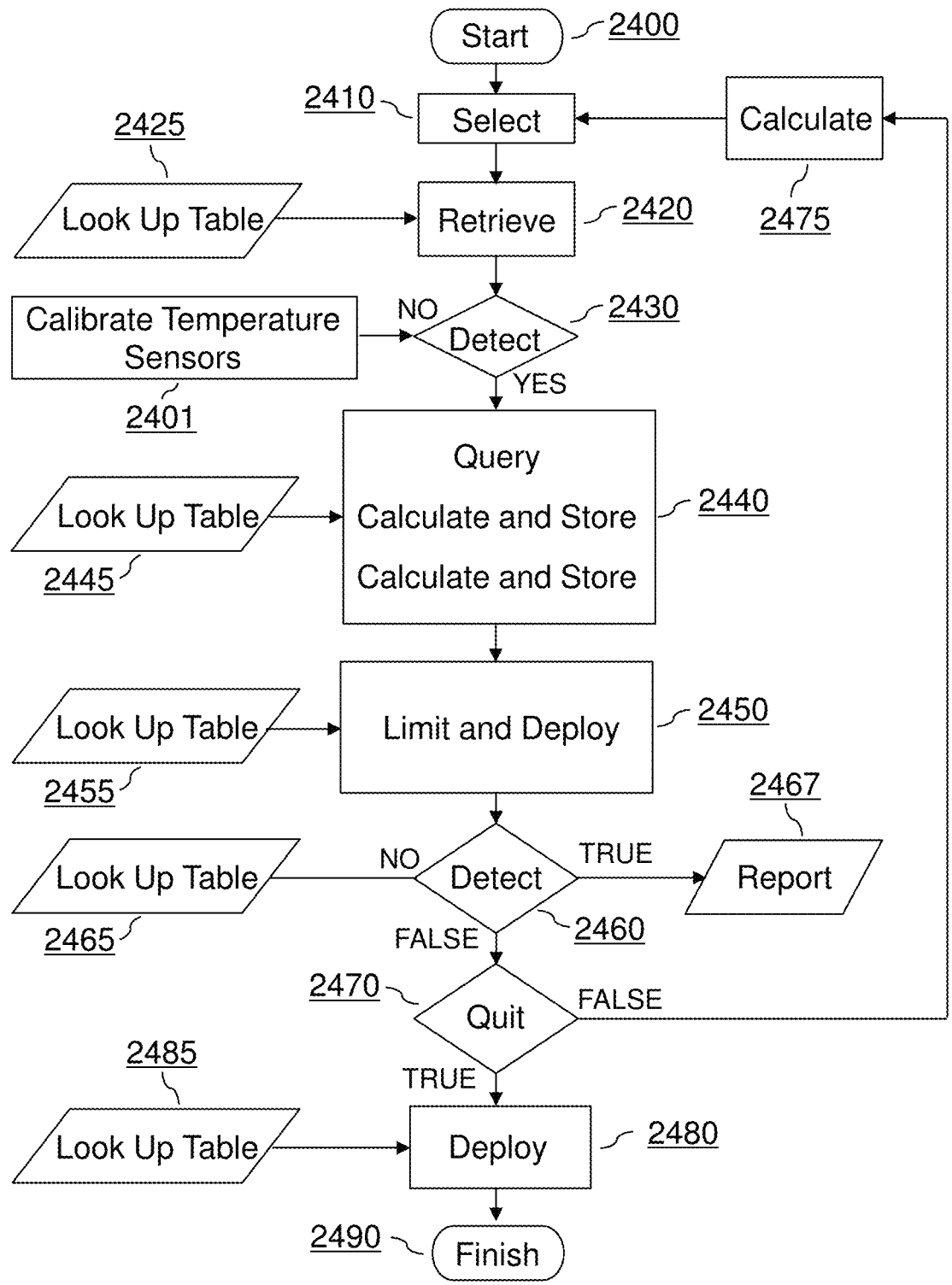
FIG. 24 is an exemplary diagram of a fan for forced-air heat exchanger control algorithm that may be used to implement aspects of certain embodiments of the present invention.

The Forced-Air Heat Exchanger Control Algorithm, shown in FIG. 24, determines the velocity of air flow over the heat exchanger that transfers heat energy between the solid heat exchanger and the gaseous atmosphere, minimizes the DC power consumption, and obscures the escaping acoustic signature.

In addition, the algorithm enables the use of low cost sensors with methods of calibration and the use of low cost FAN(s) with methods of failure detection.

Figure 27:
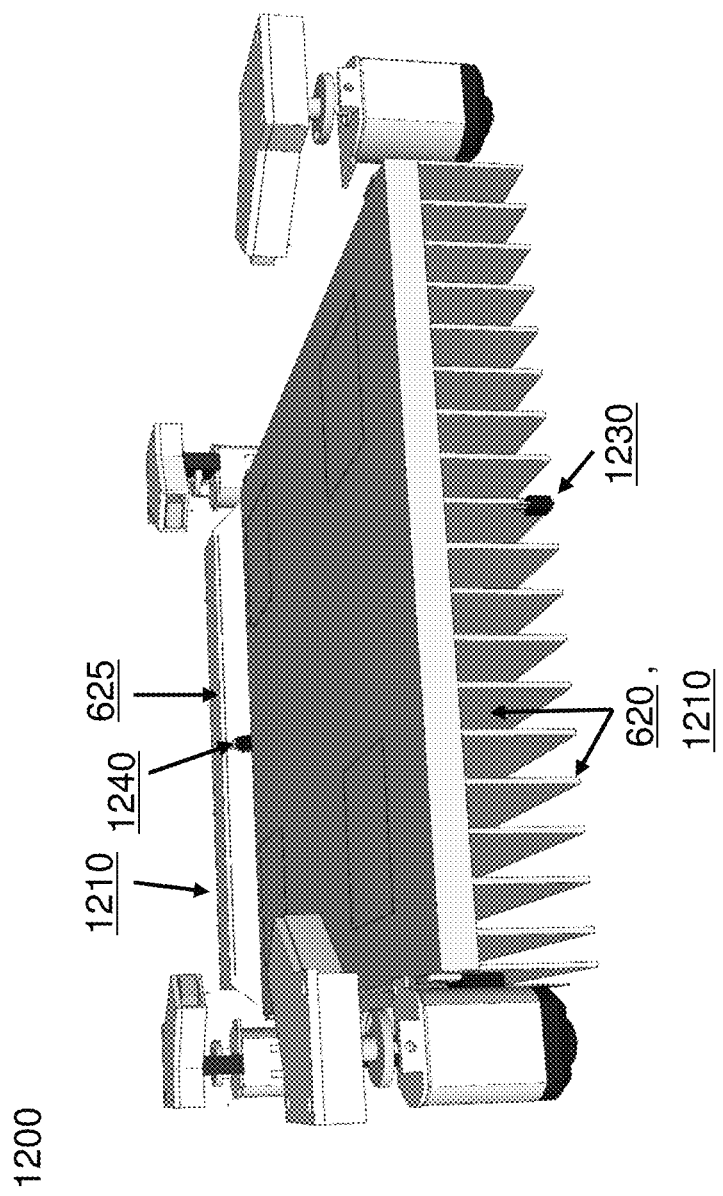
FIG. 27 is an exemplary diagram of fan control elements that may be used to implement aspects of certain embodiments of the present invention.

The control algorithm consists of nine elements (six shown in FIG. 27), eight being physical hardware and one being algorithmic software. The elements are the heat exchanger, heat exchanger inlet and outlet, forced-air-node, temperature sensors at inlet and outlet, power management unit, microprocessor, and control software.

TABLE 6

Fan Control Elements

| Reference Designator | Element | Abbreviation |
|---|---|---|
| 1200 | Forced-Air Heat Exchanger Sub-Assembly | |
| 620 | Heat Exchanger- Bottom | "HEx_Bot" |
| 1210 | Heat Exchanger- Inlet | "HEx_in" |
| 1220 | Heat Exchanger- outlet | "HEx_out" |
| 625 | Forced-Air-Node | "FAN" |
| 1230 | Temperature Sensor- Inlet | "TS_in" |
| 1240 | Temperature Sensor- outlet | "TS_out" |
| 2000 | Microprocessor (not shown in FIG. 27) | "Micro" |
| 2010 | Power Management Unit (not shown in FIG. 27) | "PMU" |
| 1250 | Control Software- Forced-Air Heat Exchanger (not shown in FIG. 27) | "Code" |

Hardware elements, when combined comprise a Forced-Air-Channel (FAC). Two primary elements, heat exchanger—bottom 620 and forced-air-node (FAN) 625 are in a physical relationship with each other. Four secondary elements, heat exchanger—inlet 1210, heat exchanger—outlet 1220, temperature sensor—inlet 1230 and temperature sensor—outlet 1240, are in physical relationship with each other as well as with the primary elements. Two additional elements, portions of the microprocessor 2000 and power management unit 2010, are not in significant physical relationship with the primary nor secondary elements.

The FAC when combined with the control software—forced-air heat exchanger 1250 element comprises a Forced-Air Heat Exchanger (FAHE).

The microprocessor 2000 queries the heat exchanger's inlet 1210 air temperature and outlet 1220 air temperature from the temperature sensor—inlet 1230 and temperature sensor—outlet 1240. Using a closed-loop control algorithm implemented in control software—forced-air heat exchanger 1250, the differential air temperature is maintained by controlling the rate of air flow over the heat exchanger—bottom 620 with the forced-air-node 625.

The control software—forced-air heat exchanger 1250 operates in two modes, the Control Mode and the Calibration mode. The following two sections describes these modes.

4.4.1 Control Mode

In Control Mode, the Control Software addresses the three goals for producing a forced-air heat exchanger design controller with low observability design. These goals are efficacy, efficiency, and obscuration. During implementation, the design recognizes three key relevant factors.

The first key relevant factor for forced-air heat exchangers (FAHE) controllers with low observability designs is that the air temperature at the outlet of a forced-air heat exchangers can be no better than the air temperature at the inlet. When the task is to remove heat from the heat exchanger, the temperature at the outlet can be no lower than the temperature at the inlet. When the task is to add heat to the heat exchanger, the temperature at the outlet can be no higher than the temperature at the inlet. An effective design ensures that the temperature differential between inlet and outlet is not too large. An efficient design ensures that the temperature differential is not too small.

Managing the temperature differential may be by use of a feed-back control loop. The process variable is the differential temperature between the outlet and inlet. The process set-point may be a temperature differential selected at design time that is not too large and not too small, optimizing between efficacy and efficiency. The process controller-output is the supply voltage to the voltage controlled FAN. The purpose of the control-loop is to drive the process variable to the process set point by adjusting the process control output. When the control loop has converged, the first two goals for low observability designs, efficacy and efficiency, have been accomplished.

The second and third key relevant factors for forced-air heat exchangers (FAHE) controllers with low observability designs are that detectors have finite observation times and that observations are more likely to occur with sharp or sudden changes. A design using obscuration techniques limits changes to the process controller output to rates slower than the attention span of the observer.

Slowly changing the acoustic and DC power signatures of the forced-air heat exchanger 1200 is accomplished with configurations of the control-loop's settling characteristic. When Proportional, Integral, and Derivative (PID) control-loop coefficients are configured for slow loop settling, the third goal for low observability, obscuration, has been accomplished.

4.4.1.1 Forced-Air Heat Exchanger Control
    Algorithm—Flow Chart (FIG. 24)

TABLE 7

Forced-Air Heat Exchanger Control Algorithm - Block Descriptions

| Reference Designator | Component Type | Description |
| --- | --- | --- |
| 2400: Start | Terminal | Start point for control algorithm is entered after User initiates the control. This is assumed to occur once User selects the food item to be stored and the atmospheric conditions are determined. i = 0 |
| 2410: Select | Process | The product design may include zero, one or more than one forced-air-channels (FAC). This process selects one of the FACs to be the current unit-under-control (UUC). The UUC is indicated by iteration variable "i". UUC[i] |
| 2420: Retrieve | Process | Retrieve the contents of the calibration look-up table for UUC. TS Cal Factors for UUC[i] |
| 2425: Look Up Table | Input/Output | Look-up table contains calibration coefficients for the UUC. TS Cal Factors[i] |
| 2430: Detect | Decision | Detect if calibration coefficients exist for UUC. If no coefficients exist, enter the Calibration Algorithm. If coefficients exist, then continue. Calibrated? |
| 2440: Query | Process | Query from the inlet temperature sensor (TS_in) and outlet temperature sensor (TS_out) the current air temperatures. Apply calibrations. TS_in[i] and TS_out[i] Calculate and store the error term (errTerm) as being the difference between the target temperature differential (TS_dTarget) and the difference between the TS_out and TS_in. errTerm[i] = (TS_dTarget[i]) − (TS_out[i] − TS_in[i]) An error term is significant and causes a change when the temperature differential between TS_out and TS_in exceeds TS_dTarget. Calculate and store the control term (ctrlFANTerm) using control-loop and PID coefficients along with the error term. ctrlFANTerm[i] = PID ( errTerm[i] ) |
| 2445: Look Up Table | Input/Output | Look-up table contains temperature differential temperature target and feed-back control-loop coefficients (PID). TS_dTarget[i] PID Terms |
| 2450: Limit and Deploy | Process | Limit the control term to not exceed functional limits, ctrlFANTermMax. Deploy limited ctrlFANTerm to Power Management Unit. ctrlFanTerm[i] = min( ctrlFANTerm[i], ctrlFANTermMax[i] ) |
| 2455: Look Up Table | Input/Output | Look-up table contains the maximum setting allowed for the FAN, ctrlFANTermMax. ctrlFANTermMax[i] |
| 2460: Detect | Decision | Test calculated ctrlFANTerm and limited ctrlFANTerm to determine if the control loop is failing to converge, suggesting that FAN is failing to provide sufficient air flow over the heat exchanger. If { ( Heat_Pumps enabled) AND. ( ctrlFANTerm[i] > ctrlFANTermMax[i] * ctrlFANTermFailFactor[i] ) AND. ( errTerm[i] ~= 0 ) . } UUC[i] failure? |
| 2465: Look Up Table | Input/Output | Look-up table contains the maximum setting allowed for the FAN, ctrlFANTermMax and factor for considering when failure has occurred, ctrlFANTermFailFactor. ctrlFANTermMax[i] ctrlFANTermFailFactor[i] |
| 2467: Report | Input/Output | Report if UUC[i] failed |
| 2470: Quit | Decision | If this control algorithm is not issued a Quit from a higher process, then continue control algorithm with next UUC. If control algorithm is issued a Quit, then discontinue control algorithm. Ctrl Algo? |
| 2475: Calculate | Process | The product design may include zero, one or more than one forced-air-channels (FAC). This process calculates new value for iteration variable "i". i = mod( i + 1, numUUCMax ) |
| 2480: Deploy | Process | When discontinuing the control algorithm, deploy ctrlFANTermMin to Power Management Unit, disabling all FANs. ctrlFANTerm[i] = ctrlFANTermMin[i] |
| 2485: Look Up Table | Input/Output | Look-up table contains the minimum setting allowed for the FAN, ctrlFANTermMin. ctrlFANTermMin[i] |
| 2490: Finish | Terminal | Finish point for control algorithm is entered after User terminates the control. This is assumed to occur when User sets the product to Stand-by mode. |

TABLE 8

| Parameter List for Control Mode | | | |
|---|---|---|---|
| Name | Symbol | Description | Units |
| Temperature Sensor Calibration Factor | TS Cal Factors[i] | Calibration factor for temperature sensor located at outlet of forced-air heat exchanger, TS_out[i]. This calibration factor is relative to TS_in[i]. | Celsius |
| Target delta temperature | TS_dTarget[i] | Target temperature differential between the outlet and inlet of the forced-air-channel. This differential temperature is the control-loop process set-point. | Celsius |
| Proportional, Integral, Derivative Coefficients | PID Terms[i] | Control-loop coefficients for configuration loop stability and settling characteristics. | Unitless |
| FAN Control Term - Max | ctrlFANTermMax[i] | The maximum operational control setting allowed for the FAN[i]. | Volts |
| FAN Control Term Fail Factor | ctrlFANTermFailFactor[i] | The multiplication factor used to determine when UUC[i] has failed. | Unitless |
| FAN Control Term - Min | ctrlFANTermMin[i] | The minimum operational control setting allowed for the FAN[i]. | Volts |

Figure 25:
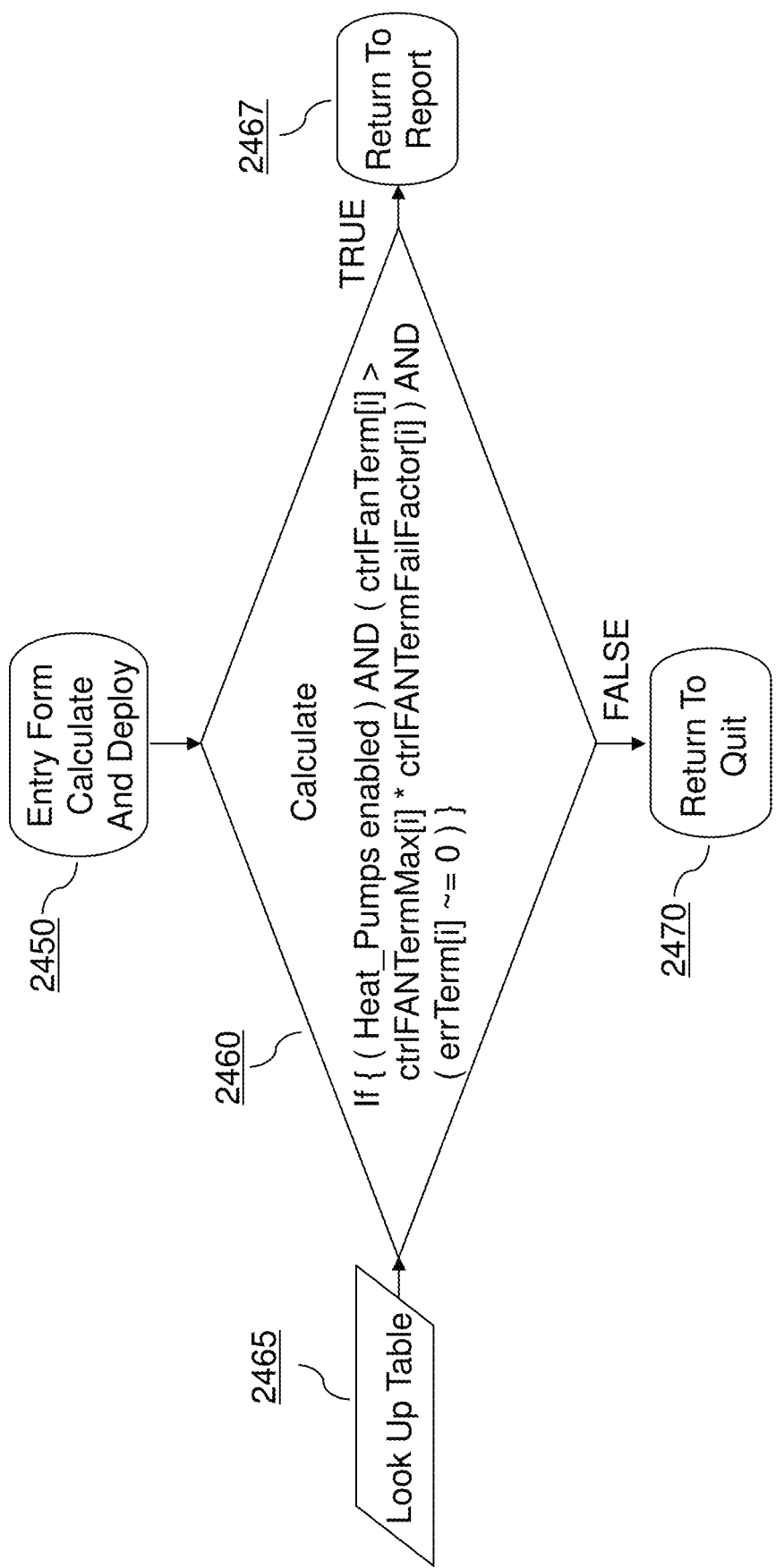
FIG. 25 is an exemplary diagram of a forced-air heat exchanger failure detection algorithm that may be used to implement aspects of certain embodiments of the present invention.

4.4.1.2 Detect Unit-Under-Control Failure—Flow Chart (FIG. 25)

In Calibration Mode, the integrity of fan functionality in the fan array may be determined using a detection algorithm.

Figure 26:
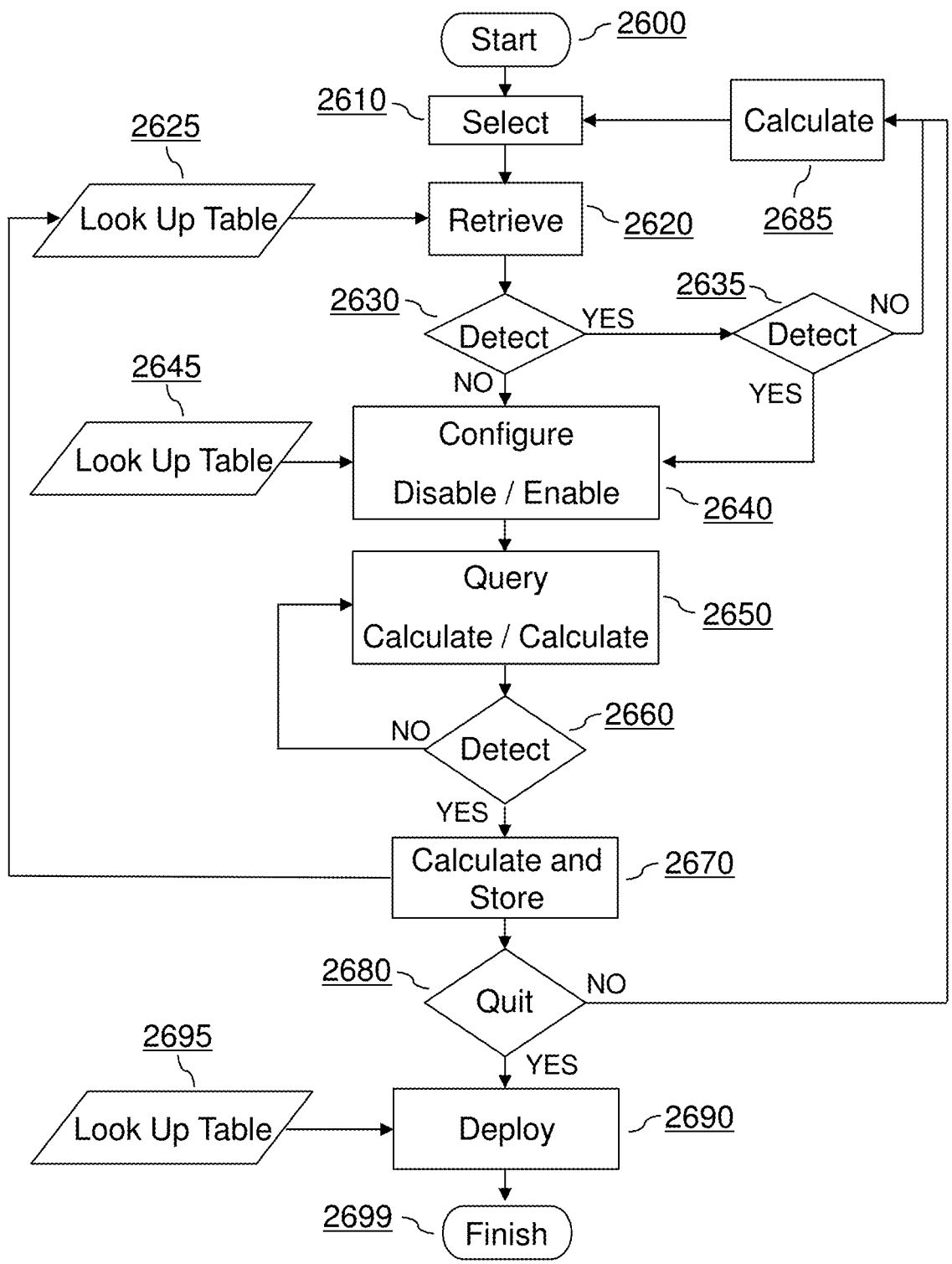
FIG. 26 is an exemplary diagram of a forced-air heat exchanger sensor calibration algorithm that may be used to implement aspects of certain embodiments of the present invention.

4.4.1.3 Forced-Air Heat Exchanger Calibration Mode—Flow Chart (FIG. 26)

In Calibration Mode, the control software configures the hardware elements to a pre-determined state and measures differential imbalances of the temperature sensors.

With the use of calibration and differential measurements during Operational Mode, low cost temperature sensors with their expected variation in temperature reporting accuracy due to production process variation may be used.

TABLE 9

| Forced-Air Heat Exchanger Calibration Mode - Block Descriptions | | |
|---|---|---|
| Reference Designator | Component Type | Description |
| 2600: Start | Terminal | Start point for calibration algorithm is entered when control algorithm detects that there are no existing calibration coefficients.<br>i = 0 |
| 2610: Select | Process | The product design may include zero, one or more than one forced-air-channels (FACs). This process selects one of the FACs to be the unit-under-control (UUC). The UUC is identified with iteration variable "i".<br>UUC[i] |
| 2620: Retrieve | Process | Retrieve the contents of the calibration look-up table for UUC.<br>TS Cal Factors for UUC[i] |
| 2625: Look Up Table | Input/Output | Look-up table contains calibration coefficients for the UUC.<br>TS Cal Factors[i] |
| 2630: Detect | Decision | Detect if calibration coefficients exist for UUC. If no coefficients exist, enter the Calibration Algorithm. If coefficients exist, then continue.<br>Calibrated? |
| 2635: Detect | Decision | Detected that calibration coefficients exist, yet re-calibration is desired.<br>Forced ReCal? |
| 2640: Configure | Process | Configure the hardware elements for calibration mode.<br>Disable All Hep[ ]<br>ctrlHEpTerm = ctrlHEpTermMin[k]<br>Ensure that all heat pumps are disabled as the calibration algorithm relies on the inlet end and outlet end of the heat exchanger to be at the same temperature.<br>Enable FAN[i] at flow rate determined by maximum flow rate and a scaling factor.<br>Enable FAN[i]<br>ctrlFANTerm = ctrlFANTermMax[i] * ctrlFANTermCalFactor[i] |

TABLE 9-continued

Forced-Air Heat Exchanger Calibration Mode - Block Descriptions

| Reference Designator | Component Type | Description |
|---|---|---|
| 2645: Look Up Table | Input/Output | Look-up table contains the maximum setting allowed for the UUC.<br>ctrlHEpTermMin[k]<br>ctrlFANTermMax[i]<br>ctrlFANTermCalFactor[ ] |
| 2650: Calculate and Deploy | Process | Query from the inlet temperature sensor (TS_in[ ]) and outlet temperature sensor (TS_out[ ]) the current air temperatures.<br>TS_in[i] and TS_out[i]<br>Calculate and store the average and standard deviation statistics from inlet and outlet temperature sensor queries.<br>AVE and STDEV of TS_out[i]<br>AVE and STDEV of TS_in[i] |
| 2660: Detect | Decision | Compare the standard deviation of the sensor queries. When standard deviations are near equal, then can assume that the inlet and outlet temperatures have settled.<br>Does STDEV(TS_out[i] = STDEV(TS_in[i]) |
| 2670: Calculate and Store | Decision | Calculate calibration coefficients and store in Look-Up Table.<br>calFactor[i] = AVE(TS_out[i]) − AVE(TS_in[i]) |
| 2680: Quit | Decision | Determine if all FACs have been calibrated.<br>All TSs Calibrated? |
| 2685: Calculate | Process | Calculate<br>i = mod( i + 1, numUUCMax ) |
| 2690: Deploy | Process | When discontinuing the calibration algorithm, deploy ctrlTermMin[ ] to Power Management Unit, disabling all FANs.<br>ctrlFANTerm[i] =ctrlFANTermMin[i] |
| 2695: Look Up Table | Input/Output | Look-up table contains the minimum setting allowed for the FAN[ ].<br>ctrlFANTermMin[i] |
| 2699: Finish | Terminal | Finish point for calibration algorithm is entered after all temperature sensors associated with FACs have been calibrated and FANs have been disabled. |

TABLE 10

Forced-Air Heat Exchanger Calibration Mode - Parameter List

| Name | Symbol | Description | Units |
|---|---|---|---|
| Temperature Sensor Calibration Factor | TS Cal Factors[i] | Calibration factor for temperature sensor located at outlet of forced-air heat exchanger, TS_out[i]. This calibration factor is relative to TS_in[i]. | Celsius |
| Heat Pump Control Term - Min | ctrlHEpTermMin[i] | The minimum operational control setting allowed for the heat pump[i]. | Volts |
| FAN Control Term - Max | ctrlFANTermMax[i] | The maximum operational control setting allowed for the FAN[i]. | Volts |
| FAN Control Term Calibration Factor | ctrlFANTermCalFactor[i] | The multiplication factor used to set FAN control during calibration. | Unitless |
| FAN Control Term - Min | ctrlFANTermMin[i] | The minimum operational control setting allowed for the FAN[i]. | Volts |

5 Interface

Desired conditions within each payload chamber are not necessarily set as a single target goal. The user may enter a profile that dictates certain conditions for a certain amount of time after which a second set of conditions and duration are followed. This process may be repeated to allow for multiple sets of conditions and durations.

Another method which may be implemented with the assistance of a Cloud connection is the detection of the current state of the payload. As the payload progresses from one state to another (e.g., cold to warm), the environmental conditions may be modified to promote the process occurring in that state. The controlled environment system may also be connected to a database that contains setup information, history of performance, data from other units as well as the ability for importing of the data or exporting the data to a database.

Users may set temperature and/or humidity (if controlled) targets for each payload. They may also set a target over time or a cycle for harvest drying, curing and long-term storage. The user may be able to set and control a complex schedule of set points over a time period (create a control mask (envelope) of inputs over time) to allow an ECU to cure a coating as one example. Another example is that this system may take frozen milk through all stages of preparation for use: frozen, liquid and ready to drink, etc. There may be other types of payloads that have multistage environment requirements in order to generate a finished product such as curing for 10 days, drying for 2 days, etc. of a painted product, for example.

This interface system may allow for programming a set of multi-time period (e.g. hours, days, weeks, months, etc.) environmental conditions (e.g. temperature, humidity, light illumination, solar radiation, vibration, shock, etc.) for automated and/or semi-automated operation. For example, this may allow the user to program multi-day environmental conditions for a payload.

The user may also be able to remotely monitor the different payloads as well as the environmental conditions. The user may get status updates, alarms, or other user selectable information and may obtain them in many selectable formats (raw data, tabular, graphical, etc.).

The user may program the controlled environment system remotely as well as locally. Locally may be performed by using the LCD and/or the buttons. This may also be completed by connecting an electronic device to the unit either through a wired interface or through a wireless interface. Wireless control or monitoring may be accomplished by use of the Cloud. It may also be accomplished by using an application or by using a combination of these (cloud and application).

The control of the controlled environment system may include informing the user that the battery is about to be depleted, or inform the user how much battery life is left, for example, in number of hours left, percentage left, etc.

The unit, Cloud, or a combination of both, may contain algorithms that can predict exactly, or with some margin of error, adverse conditions and/or when the payload will reach the optimum (or set point) of target environment, such as, humidity/moisture, temperature setting, etc. The unit and/or Cloud may perform this either alone, in conjunction with a Cloud application component, or the algorithms may be completely contained in the Cloud. In addition to adverse conditions, crowd-sourced or device-sourced data collected by the Cloud may be analyzed and used to perform payload model statistical updates to hone the prediction accuracy of how long, for example, it may take for a user's payload to finish curing, drying, etc. Graphs or curves, to be shown to a user, may be generated showing the predicted temperature over time and how long it will take for the payload to reach the ideal temperature. Overlaid on or in addition to these graphs, different scenarios may be drawn to show the impact of various settings the user may change to impact when the payload may be ready; for example, engaging or disengaging Turbo mode, increasing temperature in an earlier part of the cycle and decreasing it in a later part of the cycle. Prediction models may enable the user to make intelligent choices with respect to battery life and when the payload may be ready. For instance, it may be desired by the user to have the payload ready to use for an important social event or party.

6 Applications (Controlled Environment System, Cloud, and User-Device Based)

An application may be used with an electronic device, belonging to the user, that is coupled to the unit. The electronic device may be a laptop, mobile phone, or any other computer-type device. This application can recommend settings to a user based on the type and amount of payload that is being stored in the environment. For example, if milk were being stored, the application may recommend a temperature setting, as well as other settings for best storage results. The application may then even program the unit with these settings. The user may also take these recommendations and enter them into the unit using the LCD, the buttons, or a combination of these to program the setpoint for storing the payload.

The user, while using the application, may also receive various advertisements. The advertisements may be general in nature or they may have some commonality with the unit itself or the payload. For example, if the user is storing milk, they may receive an advertisement to buy baby items, or they may receive a coupon to buy baby items at a discount. The application may generate revenue based on these advertisements.

The Cloud may feature additional resources including education; such as, best milk to serve a baby, baby product education, storage of food education, curing of products education, identification of stains, recipes, etc. The information may be provided to the application via a Cloud server which gathers crowd-sourced recipes, temperature/humidity profiles, and other payload specific information.

The application, as well as the controlled environment system, may gather statistics and meta data as well as other types of data that are then provided to a Cloud server which may perform statistical analysis and data mining on how all the different controlled environment systems are performing and what they are storing. This information can be used to improve the product and/or provide general market insights; for example, how people are using the controlled environment system and what are their results, how people are using multiple payload chambers to heat milk, how people are using the controlled environment system at night, what kind of food people are heating or cooling, etc. and then used to improve the user experience.

For example, data may be collected from the payload chamber so that statistical analysis may be performed. This analysis may be used to enhance the storage process or assist later in a future process by the user or anyone that has access to this analysis.

Certain figures in this specification are flow charts illustrating methods and systems. It will be understood that each block of these flow charts, and combinations of blocks in these flow charts, may be implemented by computer program instructions. These computer program instructions may be loaded onto a computer or other programmable apparatus to produce a machine, such that the instructions that execute on the computer or other programmable apparatus create structures for implementing the functions specified in the flow chart block or blocks. These computer program instructions may also be stored in computer-readable memory that can direct a computer or other programmable apparatus to function in a particular manner, such that the instructions stored in computer-readable memory produce an article of manufacture including instruction structures that implement the function specified in the flow chart block or blocks. The computer program instructions may also be loaded onto a computer or other programmable apparatus to cause a series of operational steps to be performed on the computer or other programmable apparatus to produce a computer-implemented process such that the instructions that execute on the computer or other programmable apparatus provide steps for implementing the functions specified in the flow chart block or blocks.

Accordingly, blocks of the flow charts support combinations of structures for performing the specified functions and combinations of steps for performing the specified functions. It will also be understood that each block of the flow charts, and combinations of blocks in the flow charts, can be implemented by special purpose hardware-based computer systems that perform the specified functions or steps, or combinations of special purpose hardware and computer instructions.

For example, any number of computer programming languages, such as C, C++, C# (CSharp), Perl, Ada, Python, Pascal, SmallTalk, FORTRAN, assembly language, and the like, may be used to implement aspects of the present invention. Further, various programming approaches such as procedural, object-oriented or artificial intelligence techniques may be employed, depending on the requirements of each particular implementation. Compiler programs and/or virtual machine programs executed by computer systems generally translate higher level programming languages to generate sets of machine instructions that may be executed by one or more processors to perform a programmed function or set of functions.

In the foregoing descriptions, certain embodiments are described in terms of particular data structures, preferred and optional enforcements, preferred control flows, and examples. Other and further application of the described methods, as would be understood after review of this application by those with ordinary skill in the art, are within the scope of the invention.

The term "machine-readable medium" should be understood to include any structure that participates in providing data that may be read by an element of a computer system. Such a medium may take many forms, including but not limited to, non-volatile media, volatile media, and transmission media. Non-volatile media include, for example, optical or magnetic disks and other persistent memory such as devices based on flash memory (such as solid-state drives, or SSDs). Volatile media include dynamic random access memory (DRAM) and/or static random access memory (SRAM). Transmission media include cables, wires, and fibers, including the wires that comprise a system bus coupled to a processor. Common forms of machine-readable media include, for example and without limitation, a floppy disk, a flexible disk, a hard disk, a solid-state drive, a magnetic tape, any other magnetic medium, a CD-ROM, a DVD, or any other optical medium.

The data structures and code described in this detailed description are typically stored on a computer readable storage medium, which may be any device or medium that can store code and/or data for use by a computer system. This includes, but is not limited to, magnetic and optical storage devices such as disk drives, magnetic tape, CDs (compact discs) and DVDs (digital versatile discs or digital video discs), and computer instruction signals embodied in a transmission medium (with or without a carrier wave upon which the signals are modulated). For example, the transmission medium may include a communications network, such as the Internet.

Figure 28:
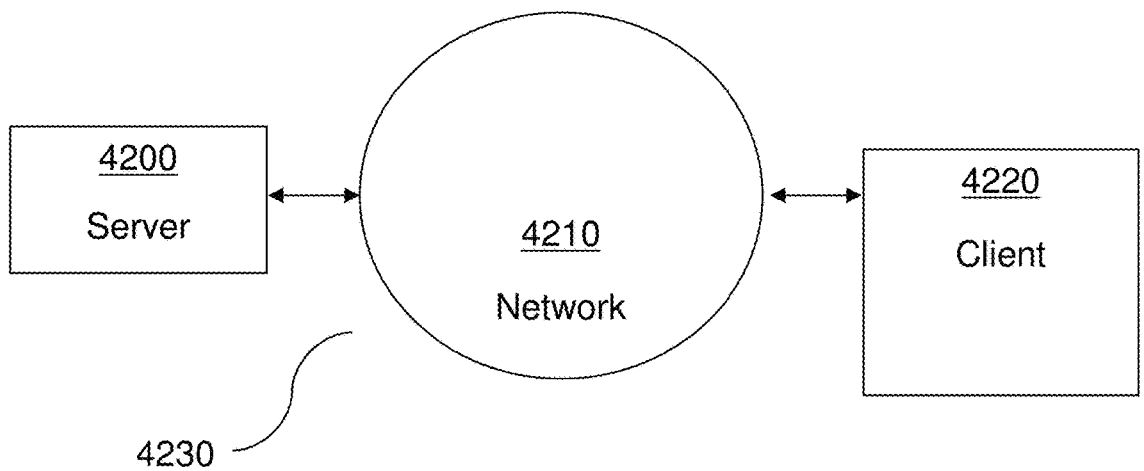
FIG. 28 illustrates an exemplary networked computing system environment and its relevant components according to certain embodiments of the present invention.

FIG. 28 depicts an exemplary networked environment 4230 in which systems and methods, consistent with exemplary embodiments, may be implemented. As illustrated, networked environment 4230 may include, without limitation, a server (4200), a client (4220), and a network (4210). The exemplary simplified number of servers (4200), clients (4220), and networks (4210) illustrated in FIG. 28 can be modified as appropriate in a particular implementation. In practice, there may be additional servers (4200), clients (4220), and/or networks (4210).

In certain embodiments, a client 4220 may connect to network 4210 via wired and/or wireless connections, and thereby communicate or become coupled with server 4200, either directly or indirectly. Alternatively, client 4220 may be associated with server 4200 through any suitable tangible computer-readable media or data storage device (such as a disk drive, CD-ROM, DVD, or the like), data stream, file, or communication channel.

Network 4210 may include, without limitation, one or more networks of any type, including a Public Land Mobile Network (PLMN), a telephone network (e.g., a Public Switched Telephone Network (PSTN) and/or a wireless network), a local area network (LAN), a metropolitan area network (MAN), a wide area network (WAN), an Internet Protocol Multimedia Subsystem (IMS) network, a private network, the Internet, an intranet, a cellular network, and/or another type of suitable network, depending on the requirements of each particular implementation.

One or more components of networked environment 4230 may perform one or more of the tasks described as being performed by one or more other components of networked environment 4230.

Figure 29:
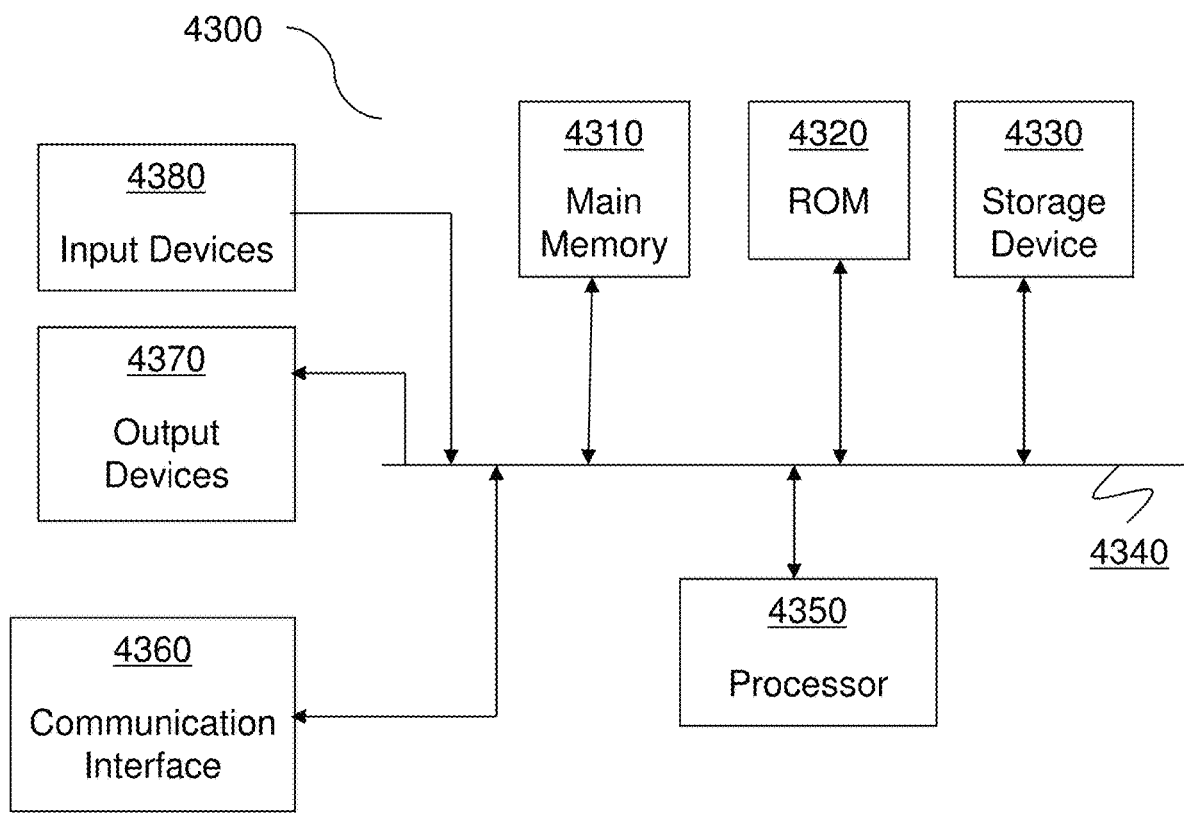
FIG. 29 is an exemplary block diagram of a computing device that may be used to implement aspects of certain embodiments of the present invention.

FIG. 29 is an exemplary diagram of a computing device 4300 that may be used to implement aspects of certain embodiments of the present invention, such as aspects of server 4300 or of client 4320, or of the environmental control unit embodiments described in this document. In certain embodiments, computing device 4300 may be, without limitation, a desktop or notebook computing device, or a mobile computing device that may include, without limitation, a smart phone or tablet device, or it may be integrated entirely or partially into an environmental control unit. Computing device 4300 may include, without limitation, a bus 4340, one or more processors 4350, a main memory 4310, a read-only memory (ROM) 4320, a storage device 4330, one or more input devices 4380, one or more output devices 4370, and a communication interface 4360. Bus 4340 may include, without limitation, one or more conductors that permit communication among the components of computing device 4300.

Processor 4350 may include, without limitation, any type of conventional processor, microprocessor, or processing logic that interprets and executes instructions. Main memory 4310 may include, without limitation, a random-access memory (RAM) or another type of dynamic storage device that stores information and instructions for execution by processor 4350. ROM 4320 may include, without limitation, a conventional ROM device or another type of static storage device that stores static information and instructions for use by processor 4350. Storage device 4330 may include, without limitation, a magnetic and/or optical recording medium and its corresponding drive.

Input device(s) 4380 may include, without limitation, one or more conventional mechanisms that permit a user to input information to computing device 4300, such as a keyboard, a mouse, a pen, a stylus, handwriting recognition, voice recognition, biometric mechanisms, touch screen, and the like. Output device(s) 4370 may include, without limitation, one or more conventional mechanisms that output information to the user, including a display, a projector, an A/V receiver, a printer, a speaker, and the like. Communication interface 4360 may include, without limitation, any transceiver-like mechanism that enables computing device 4300 to communicate with other devices and/or systems. For example, communication interface 4360 may include, without limitation, mechanisms for communicating with another device or system via a network.

As described in detail herein, computing device 4300 may perform operations based on software instructions that may be read into memory 4310 from another computer-readable medium, such as data storage device 4330, or from another device via communication interface 4360. The software instructions contained in memory 4310 cause processor 4350 to perform processes that are described elsewhere. Alternatively, hardwired circuitry may be used in place of, or in combination with, software instructions to implement processes consistent with the present invention. Thus, various implementations are not limited to any specific combination of hardware circuitry and software.

Details regarding the foregoing components, which may be implemented in a single computing device or distributed among multiple computing devices, are described throughout this document.

Those skilled in the art will realize that embodiments of the present invention may use any suitable data communication network, including, without limitation, direct point-to-point data communication systems, dial-up networks, personal or corporate intranets, proprietary networks, or combinations of any of these with or without connections to the Internet.

While the above description contains many specifics and certain exemplary embodiments have been described and shown in the accompanying drawings, it is to be understood that such embodiments are merely illustrative of and not restrictive on the broad invention, and that this invention not be limited to the specific constructions and arrangements shown and described, since various other modifications may occur to those ordinarily skilled in the art, as mentioned above. The invention includes any combination or subcombination of the elements from the different species and/or embodiments disclosed herein.

What is claimed is:

1. A controlled environment system, comprising:
an enclosure comprising a plurality of environmental control units, a user interface, a controller, and a heat exchanger;
wherein each of said environmental control units comprises a payload chamber and is coupled to said controller and to said heat exchanger;
wherein each of said payload chambers encloses a respective payload and comprises a removable cover;
wherein each of said environmental control units is programmable via said user interface to cool said respective payload within said payload chamber of said environmental control unit to a first cooling temperature below an ambient temperature or to heat said respective payload within said payload chamber of said environmental control unit to a second heating temperature above said ambient temperature;
and wherein said heat exchanger is shared by said plurality of environmental control units such that said controller causes a portion of heat removed from a first one of said plurality of environmental control units to be added to a second one of said plurality of environmental control units.

2. The controlled environment system of claim 1, wherein each of said payload chambers comprises a heat transfer liner.

3. The controlled environment system of claim 2, wherein each of said heat transfer liners is conformable to the shape of the respective payload.

4. The controlled environment system of claim 1, wherein each of said payload chambers is configured to be user removable from said enclosure.

5. The controlled environment system of claim 1, wherein each of said payloads comprises a bottle for holding a liquid.

6. The controlled environment system of claim 5, wherein each of said environmental control units is further programmable to substantially sterilize said bottle within said respective payload chamber.

7. The controlled environment system of claim 6, wherein said sterilization comprises circulation of steam within said respective payload chamber.

8. The controlled environment system of claim 1, further comprising a plurality of agitators, wherein each of said agitators is coupled to said controller and to one of said payload chambers.

9. The controlled environment system of claim 1, wherein each of said environmental control units further comprises a reversible current thermoelectric device coupled to said controller.

10. The controlled environment system of claim 3, wherein each of said environmental control units further comprises a reversible current thermoelectric device coupled to said controller.

11. The controlled environment system of claim 1, wherein each of said environmental control units further comprises a temperature sensor coupled to a respective payload chamber of said environmental control unit and to said controller.

12. The controlled environment system of claim 6, wherein said sterilization comprises ultraviolet light radiation within said respective payload chamber.

* * * * *